US011066423B2

(12) United States Patent
Clouatre et al.

(10) Patent No.: US 11,066,423 B2
(45) Date of Patent: Jul. 20, 2021

(54) MONOMERIC BIMETAL HYDROXYCITRIC ACID COMPOUNDS AND METHODS OF MAKING AND USING THE SAME

(71) Applicant: GLYKON TECHNOLOGIES GROUP, LLC, Seattle, WA (US)

(72) Inventors: Daniel E. Clouatre, Seattle, WA (US); Nimpan Bangun, Seattle, WA (US); Dallas L. Clouatre, Seattle, WA (US)

(73) Assignee: GLYKON TECHNOLOGIES GROUP, LLC, Seattle, WA (US)

( * ) Notice: Subject to any disclaimer, the term of this patent is extended or adjusted under 35 U.S.C. 154(b) by 0 days.

(21) Appl. No.: 16/869,097

(22) Filed: May 7, 2020

(65) Prior Publication Data

US 2020/0331930 A1  Oct. 22, 2020

Related U.S. Application Data

(63) Continuation of application No. 15/699,706, filed on Sep. 8, 2017, now abandoned.

(60) Provisional application No. 62/384,963, filed on Sep. 8, 2016.

(51) Int. Cl.
*C07F 3/02* (2006.01)
*C07F 3/00* (2006.01)
*C07F 13/00* (2006.01)

(52) U.S. Cl.
CPC .......... *C07F 3/02* (2013.01); *C07F 3/003* (2013.01); *C07F 13/005* (2013.01)

(58) Field of Classification Search
CPC .................................................. C07C 59/265
USPC .......................................... 562/584; 514/574
See application file for complete search history.

(56) References Cited

U.S. PATENT DOCUMENTS

| | | | |
|---|---|---|---|
| 6,160,172 A | 12/2000 | Balasubramanyam et al. | |
| 6,207,714 B1 | 3/2001 | Clouatre et al. | |
| 6,441,041 B1 | 5/2002 | Clouatre et al. | |
| 6,447,807 B1 | 9/2002 | Clouatre et al. | |
| 6,476,071 B1 | 11/2002 | Clouatre et al. | |
| 6,482,858 B1 | 11/2002 | Clouatre et al. | |
| 7,015,250 B2 | 3/2006 | Clouatre et al. | |
| 7,189,416 B2 | 3/2007 | Clouatre et al. | |
| 7,943,186 B2 | 5/2011 | Raju | |
| 8,367,864 B2 | 2/2013 | Moffett et al. | |
| 8,394,856 B2 | 3/2013 | Clouatre | |
| 9,789,076 B2 * | 10/2017 | Clouatre | A61K 36/42 |
| 10,376,483 B2 * | 8/2019 | Clouatre | A61K 9/145 |
| 10,561,630 B2 * | 2/2020 | Clouatre | A61K 9/2054 |
| 2004/0219124 A1 | 4/2004 | Gupta | |
| 2005/0009919 A1 | 1/2005 | Clouatre | |
| 2005/0032901 A1 | 2/2005 | Clouatre | |
| 2006/0025482 A1 | 2/2006 | Clouatre | |
| 2006/0074108 A1 | 4/2006 | Gupta | |
| 2006/0141030 A1 | 6/2006 | Clouatre et al. | |
| 2006/0228412 A1 | 10/2006 | Clouatre et al. | |
| 2008/0145408 A1 | 6/2008 | Moffett | |
| 2008/0293815 A1 | 11/2008 | Clouatre | |
| 2010/0152488 A1 * | 6/2010 | Rao | C07C 59/245 562/584 |
| 2010/0273884 A1 | 10/2010 | Clouatre et al. | |
| 2010/0323031 A1 | 12/2010 | Clouatre | |
| 2011/0003986 A1 | 1/2011 | Moffett et al. | |
| 2011/0105600 A1 | 5/2011 | Clouatre et al. | |
| 2011/0274654 A1 | 11/2011 | Bahadoor | |
| 2013/0028969 A1 | 1/2013 | Clouatre et al. | |
| 2013/0150448 A1 | 6/2013 | Moffett et al. | |
| 2017/0312200 A1 | 11/2017 | Saeki | |
| 2018/0110750 A1 | 4/2018 | Clouatre | |

FOREIGN PATENT DOCUMENTS

| | | |
|---|---|---|
| JP | 2014218442 | 11/2014 |
| WO | WO 99/03464 | 1/1999 |
| WO | WO 2000/048983 | 8/2000 |
| WO | WO 2004/100682 | 11/2004 |
| WO | WO 2004/105733 | 12/2004 |
| WO | WO 2005/002565 | 1/2005 |
| WO | WO 2005/007152 | 1/2005 |
| WO | WO 2005/025544 | 3/2005 |
| WO | WO 2005/030195 | 4/2005 |

(Continued)

OTHER PUBLICATIONS

Pccompound-selected items 1-5, Create Date Aug. 8, 2005 to Feb. 12, 2015.*
CAS Abstract of Y. Kobayashi et al. JP-2014218442 (2014).
Goudarzvand et al. "Hydroxycitric acid ameliorates inflammation and oxidative stress in mouse models of multiple sclerosis", Neural Regeneration Research, Oct. 2016, vol. 11, Issue 10, 1610-1616.
Jena et al. "Chemistry and Biochemistry of (−)-Hydroxycitric Acid from Garcinia" J. Agric. Food Chem., 2002, 50 (1), pp. 10-22.
Koybayashi Machine Translation of JP-2014218442 (2014).
Lang et al., "An equation to calculate internuclear distances of covalent, ionic and metallic lattices" Phys. Chem. Chem. Phys. (2015) 17:3355-3369.

(Continued)

*Primary Examiner* — Erich A Leeser
(74) *Attorney, Agent, or Firm* — Karl Bozicevic; Bozicevic, Field & Francis LLP

(57) ABSTRACT

Monomeric bimetal hydroxycitric acid (HCA) compounds are provided. The subject compounds include a divalent metal (X) bonded to the carboxylic acids of C2 and C3 and a monovalent metal (Y) bonded to the carboxylic acid of C1. Also provided are methods of preparing the subject compounds from a dimeric starting material (e.g., $X_3(HCA)_2$) which include acidifying the dimer to produce a monomeric intermediate which is subsequently neutralized with YOH base. Methods of alleviating at least one symptom associated with a target disease or condition in a subject are provided. Also provided are compositions including the subject monomeric bimetal HCA compounds which find use in a variety of therapeutic applications.

18 Claims, 4 Drawing Sheets

(56) References Cited

FOREIGN PATENT DOCUMENTS

WO    WO 2008/048574      4/2008
WO    WO 2008/140444     11/2008

OTHER PUBLICATIONS

Lenglet, M. "Iono-Covalent Character of the Metal-Oxygen Bonds in Oxides: A Comparison of Experimental and Theoretical Data" Active and Passive Elec. Com. (Mar. 2004) 27:1-60.
Mortimer, Robert G., "The Electronic State of Molecules" Physical Chemistry (2004) pp. 647-719.
Preiss et al., "Is Universal, Simple Melting Point Prediction Possible?" Chem Phys Chem Phys (2011) 12:2959-2972.
Pubchem, Substance Record for SID 228792826, Available date: Feb. 12, 2015 [retrieved on Oct. 13, 2017] Retrieved from the Internet: ,URL:https://pubchem.ncbi.nlm.nih.gov/228792826. Entire document.
Rao et al., "Hydroxycitric acid lactone and its salts: Preparation and appetite suppression studies", Food Chemistry, vol. 120, Issue 1, May 1, 2010, pp. 235-239.
Sullivan et al., "Metabolic regulation as a control for lipid disorders. I. Influence of (--)-hydroxycitrate on experimentally induced obesity in the rodent." American Journal of Clinical Nutrition 1977; 30: 767-776.

\* cited by examiner

MONOMERIC BIMETAL HYDROXYCITRIC ACID COMPOUNDS AND METHODS OF MAKING AND USING THE SAME

CROSS REFERENCE TO RELATED APPLICATION

This application is a continuation of U.S. patent application Ser. No. 15/699,706, filed Sep. 8, 2017, which pursuant to 35 U.S.C. § 119(e), claims priority to U.S. Provisional Application No. 62/384,963, filed Sep. 8, 2016, which applications are incorporated herein by reference.

INTRODUCTION

Hydroxycitric acid (HCA) is a derivative of citric acid found in the fruit of members of the plant genus *Garcinia*. There are four isomers of, (+)- and (−)-hydroxycitric acid, and (+)- and (−)-allo-hydroxycitric acid. The (−)-hydroxycitric acid isomer is the one found in *Garcinia* (see e.g., Jena et al. "Chemistry and Biochemistry of (−)-Hydroxycitric Acid from *Garcinia*." Journal of Agricultural and Food Chemistry 50(1):10-22). Free HCA can be present in solution in an acid form and/or a lactone form. Calcium, magnesium and potassium salts of HCA are described, e.g., in U.S. Pat. Nos. 8,394,856 and 7,943,186. Compositions including calcium HCA and sodium HCA salts have been sold commercially since 1994.

(−)-HCA is a potent inhibitor of ATP citrate lyase (EC 4.1.3.8), which catalyzes the extramitochondrial cleavage of citrate to oxaloacetate and acetyl-CoA. The inhibition of this reaction limits the availability of acetyl-CoA units required for fatty acid synthesis and lipogenesis during a lipogenic diet. HCA can have several biological effects (Jena et al. "Chemistry and Biochemistry of (−)-Hydroxycitric Acid from *Garcinia*" J. Agric. Food Chem., 2002, 50 (1), pp 10-22). HCA can affect the metabolic and other physiologic functions of mammals, including humans. HCA, as well as several synthetic derivatives of citric acid, can inhibit the production of fatty acids from carbohydrates, suppress appetite and inhibit weight gain (Sullivan et al., American Journal of Clinical Nutrition 1977; 30: 767). Numerous other benefits have been attributed to the use of HCA, including, but not limited to, an increase in the metabolism of fat stores for energy and an increase in thermogenesis, and wound healing.

A number of different HCA salt forms and compositions have been investigated. Potassium HCA and sodium HCA salt forms are extremely hygroscopic. The therapeutic use of HCA salts is limited by poor absorption and chemical instability at acidic pH, e.g., inactivation of HCA salts via lactonization upon exposure to the acidic milieu of prepared drinks and the mammalian gut. Some calcium salts of HCA exhibit especially poor bioavailability. Particular double and triple-metal salt compositions prepared using conventional methods exhibit similarly poor bioavailability despite improved solubility. For example, a peak blood plasma HCA concentration was reached in subjects approximately 2 hours after administration of Super Citrimax potassium/calcium (−)-hydroxycitrate, indicating only partial absorption of HCA by the subjects. See also, Anal. Biochem., 2001 May 1; 292(1): 148-54; and FASEB Journal 15; 4:632, Abs. 501.1, 2001, 38.

Dosages of various HCA compositions found to be effective are quite large, indeed beyond the normal range for pharmaceutical products, with efficacy that is highly variable. The effective dose at which HCA is found to significantly decrease de novo lipogenesis (DNL) in rats is 1.32 mmol/kg/day or 0.27 g/kg/day (Lipids. 1974 February; 9(2):121-8) This extrapolates to approximately 4.5 g/day for a 70 kg human being. One study with obese subjects indicated that administering 6 g HCA/day for 5 days failed to inhibit DNL or to promote fatty acid oxidation Anal Biochem. 2001 May 1; 292(1):148-54). A later study found a significant, yet limited effect after 7 days of a diet designed specifically to induce de novo lipogenesis in humans. (Physiol Behav. 2006 Jul. 30; 88(4-5):371-81). See also, Nutr Metab (Lond). 2005 Sep. 13; 2:23.

Experimental work with animals has demonstrated considerable differences in both efficacy and modes of action among the various conventional HCA salt forms.

SUMMARY

Monomeric bimetal hydroxycitric acid (HCA) compounds are provided. The subject compounds include a divalent metal (X) bonded to the carboxylic acids of C2 and C3 and a monovalent metal (Y) bonded to the carboxylic acid of C1. Also provided are methods of preparing the subject compounds from a dimeric starting material (e.g., $X_3(HCA)_2$) which include acidifying the dimer to produce a monomeric intermediate which is subsequently neutralized with YOH base. Methods of alleviating at least one symptom associated with a target disease or condition in a subject are provided. Also provided are compositions including the subject monomeric bimetal HCA compounds which find use in a variety of therapeutic applications.

DEFINITIONS

Figure 1:
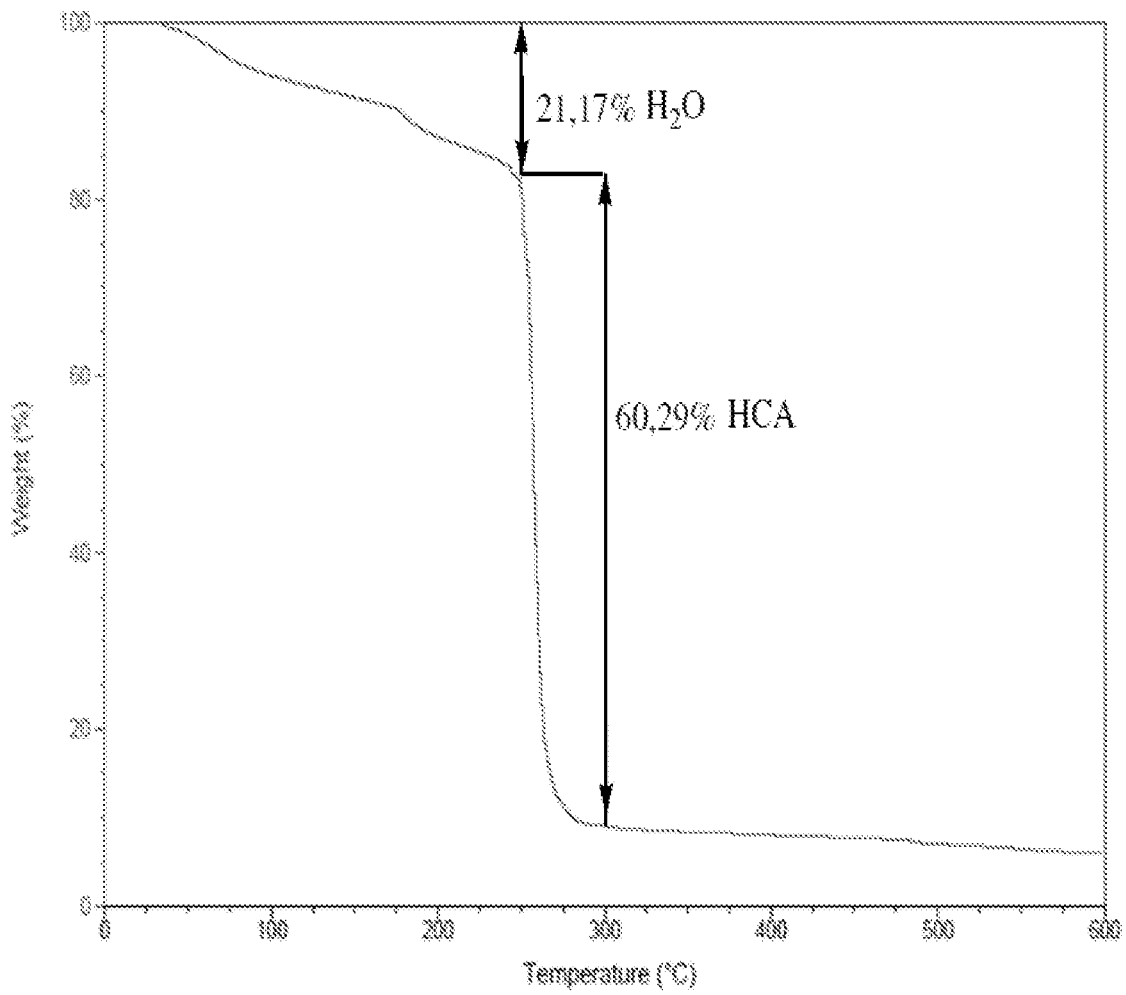
FIG. 1 shows thermal gravimetric analysis (TGA) analysis of an exemplary monomeric KMgHCA compound.

Before describing exemplary embodiments in greater detail, the following definitions are set forth to illustrate and define the meaning and scope of the terms used in the description. Any undefined terms have their art recognized meanings.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

As used herein, the terms "bimetal HCA" and "HCA metal compound" are used interchangeably to refer to the subject compounds and compositions that include HCA and two metal atoms bonded to the HCA. The two metal atoms can be considered two distinct and different metal ions (e.g., a first divalent metal and a second monovalent metal) that form individual bonds to groups of the HCA molecule that can have significant covalent character. The ratio of HCA to the two metal atoms can be 1:1:1.

A heterocyclic compound or ring structure is a cyclic compound or structure that has atoms of at least two different elements as members of its ring(s), e.g., a carbon atom and at least one atom selected from a N, O or S atom.

The terms divalent and bivalent refer to an atom, metal, ion, functional group, or molecule that has a valence of two. Valency is the number of chemical bonds formed, which may be covalent or ionic.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

Bioavailability is a subcategory of absorption and is the fraction of an administered dose of unchanged drug that reaches the systemic circulation. The terms absorption and uptake refer to the process of transport of a compound from the intestinal or gut lumen into the systemic circulation.

Also of interest as active agents for use in embodiments of the methods are prodrugs. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein suitable for the methods and compositions of the present disclosure. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, succinates, and ethylsuccinates.

Other definitions of terms may appear throughout the specification.

DETAILED DESCRIPTION

Before the present compounds, formulations, methods of preparation and uses are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a compound" includes a plurality of such compounds and reference to "the reaction" includes reference to one or more reactions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Monomeric Bimetal HCA Compounds

Aspects of the present disclosure include monomeric bimetal compounds of hydroxycitric acid (HCA) that include two metals, e.g., a first divalent metal ion and a second monovalent metal ion. In some instances, the compound is a bimetal heterocyclic compound of HCA exhibiting covalent characteristics, e.g., where the bonds between metal ions and the HCA exhibit covalent characteristics. The subject HCA-derived compounds, methods of synthesis, as well as examples of their physiologic uses along with showings of in vivo activity are disclosed and described herein.

The structures and physical and chemical properties of the subject monomeric bimetal HCA compounds differ from those of known HCA salts and mixtures of HCA salts, even those that include similar metal ions, proportions of the HCA and metals, as well as similar pH conditions. In some cases, the conventional HCA salts form multimeric structures. HCA includes three saturated carbon atoms (C1-C3), each substituted with a carboxylic acid (—CO$_2$H), and where C1 and C2 are further substituted with hydroxy groups. The C1 carboxylic acid has a more acidic pKa as compared to the C3 carboxylic acid group (acetic acid pKa approx 4.76 versus glycolic acid pKa approx 3.83).

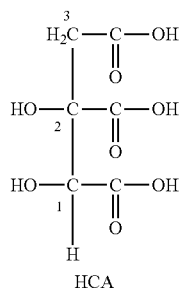

HCA

HCA isomers of interest from which the subject monomeric bimetal HCA compounds can be derived include, but are not limited to, (+)-hydroxycitric acid, (−)-hydroxycitric acid, (+)-allo-hydroxycitric acid and (−)-allo-hydroxycitric acid. In certain embodiments, the compound is derived from (−)-hydroxycitric acid.

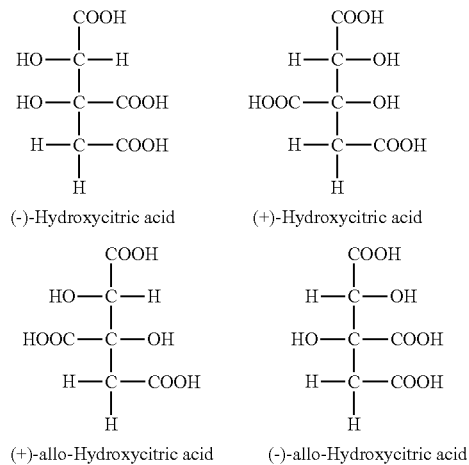

In conventional HCA preparations, HCA and salts thereof can be present/convert to a lactone form. Lactone forms of HCA include the following:

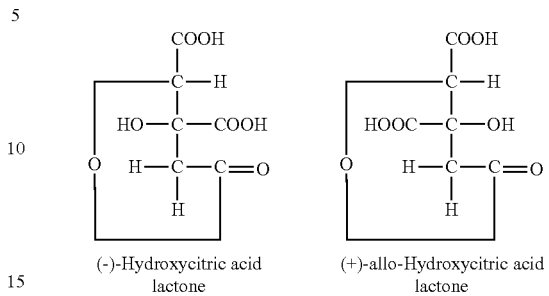

The subject methods and compounds provide for monomeric forms of HCA that do not include a lactone. The subject methods of preparation provide for selective installation of a first divalent metal and a second monovalent metal into HCA with a particular configuration of metal-HCA bonds to produce a monomeric bimetal HCA compound. The subject methods of preparation provide for preparation of monomeric compounds, e.g., a compound including one and only one molecule of HCA per first and second metal, without formation of an undesirable mixture of dimeric and/or oligomeric HCA forms. The subject methods can also provide for preparation of monomeric bimetal compounds without formation of significant amounts of a lactone form of HCA.

The first divalent metal (X) bonds to the carboxylic acid groups of C2 and C3 to form a 7-membered heterocyclic ring in the subject compound. The X—O bonds of the 7-membered heterocyclic ring can be characterized as having covalent character. In some embodiments, the X—O bonds of the 7-membered heterocyclic ring can be characterized as having substantial covalent character. By "substantial covalent character" is meant 50% or more covalent character, such as 60% or more, 70% or more, 80% or more, 90% or more, or 95% or more covalent character, as determined by any convenient method, e.g., via conductivity of an aqueous solution of the compound relative to a control, e.g., as described in the experimental section.

In addition, a monovalent metal ion (Y) is installed into the compound via bonding to the C1 carboxylic acid group. In some cases, the 7-membered heterocyclic ring is substantially stable in an aqueous environment, such that the first divalent metal (X) does not substantially dissociate from the hydroxycitric acid. In certain instances, the second monovalent metal (Y) has covalent character and does not fully dissociate from the HCA in an aqueous solution. It is understood that the bonding of the first and/or second metals to the hydroxycitric acid can be referred to as the result of bonding of carboxylate group(s) of HCA and first and second metal ions, where the bonds that are formed can be characterized as having a particular covalent character and/or a particular ionic character. In some cases, the first metal is a divalent metal that forms polar covalent bonds to the HCA. In certain cases, the second metal is a monovalent metal that forms a bond with the HCA that has partial covalent character and partial ionic character, e.g., such that the second monovalent metal can at least partially dissociate from the HCA under suitable aqueous conditions.

In some embodiments, the monomeric bimetal compound is of formula (I):

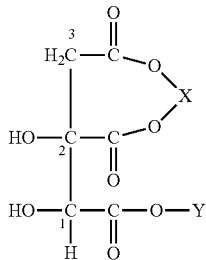

wherein X is a divalent metal and Y is a monovalent metal. In certain instances, when the subject compound is contacted with a suitable aqueous solution, the monomeric metal can dissociate from the subject monomeric bimetal compound and become hydrated to result in an ionic binary complex, e.g., as follows:

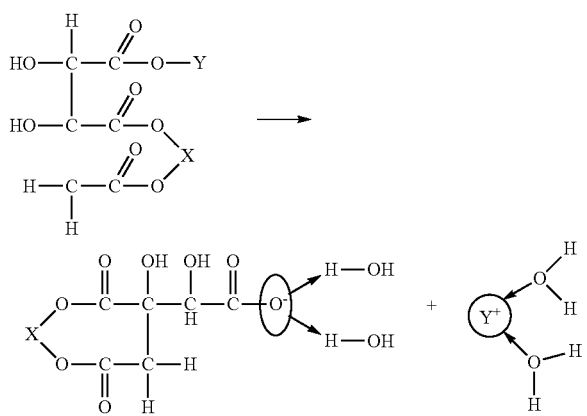

In certain embodiments, when the subject compound is contacted with an aqueous solution, no significant dissociation of the first and/or second metal from the compound occurs.

Any convenient divalent metals (X) can be utilized in the subject compounds. In some embodiments of formula (I), X is a metal selected from Group IIA metals, Group IIA metals and Group VIIA metals. It is understood that as used herein, references to groups of the periodic table correspond to the old IUPAC European system.

X can be a Group IIA metal. Group IIA metals of interest include, beryllium (Be), magnesium (Mg), calcium (Ca), strontium (Sr), barium (Ba) and radium (Ra). In certain instances of formula (I), X is selected from Mg, Ca, Sr, Ba and Ra. In certain cases of formula (I), X is Mg. In certain cases of formula (I), X is Ca. In certain cases of formula (I), X is Sr. In certain cases of formula (I), X is Ba. In certain cases of formula (I), X is Ra.

X can be a Group IIB metal. Group IIB metals of interest include, but are not limited to, zinc (Zn) and cadmium (Cd). In certain cases of formula (I), X is Zn. In certain cases of formula (I), X is Cd.

X can be a Group VIIA metal. Group VIIB metals of interest include, manganese (Mn), technetium (Tc) and rhenium (Re). In certain cases of formula (I), X is Mn. In certain cases of formula (I), X is Tc. In certain cases of formula (I), X is Re.

Any convenient monovalent metals (Y) can be utilized in the subject compounds. In some embodiments of formula (I), Y is a Group IA metal. Group IIA metals of interest include, lithium (Li), sodium (Na), potassium (K), rubidium (Rb) and cesium (Cs). In certain cases of formula (I), X is Li, Na or K. In certain cases of formula (I), X is Li. In certain cases of formula (I), X is Na. In certain cases of formula (I), X is K.

In some embodiments of formula (I), X is selected from Mg, Ca, Sr, Zn and Mn and Y is selected from Li, Na and K. In some embodiments of formula (I), X is selected from Mg, Ca, Sr, Zn and Mn and Y is Li. In some embodiments of formula (I), X is selected from Mg, Ca, Sr, Zn and Mn and Y is Na. In some embodiments of formula (I), X is selected from Mg, Ca, Sr, Zn and Mn and Y is K. In certain instances, the subject monomeric bimetal HCA compound is a compound of Table 1. In certain instances of any one of the embodiments described herein (e.g., a compound of Table 1), the HCA is (−)-hydroxycitric acid.

TABLE 1

| Compounds of interest of Formula (I) | | |
|---|---|---|
| Compound of Formula (I) | X | Y |
| 1 (LiMgHCA) | Mg | Li |
| 2 (LiCaHCA) | Ca | Li |
| 3 (LiSrHCA) | Sr | Li |
| 4 (LiZnHCA) | Zn | Li |
| 5 (LiMnHCA) | Mn | Li |
| 6 (NaMgHCA) | Mg | Na |
| 7 (NaCaHCA) | Ca | Na |
| 8 (NaSrHCA) | Sr | Na |
| 9 (NaZnHCA) | Zn | Na |
| 10 (NaMnHCA) | Mn | Na |
| 11 (KMgHCA) | Mg | K |
| 12 (KCaHCA) | Ca | K |
| 13 (KSrHCA) | Sr | K |
| 14 (KZnHCA) | Zn | K |
| 15 (KMnHCA) | Mn | K |

In some embodiments, X=Ca and Mg, e.g., referred as KCaHCA.3H$_2$O and KMgHCA.8H$_2$O. Group IIA metals of interest include Be, Mg, Ca, Sr, Ba and Ra, e.g., having ionic radii of Be$^{2+}$ (0.31 A°), Mg (0.65 A°) and Ca$^{2+}$ (0.92 A°). Because of small radii of Be$^{2+}$, Be(OH)$_2$ has very high covalent character therefore it is sparingly soluble in water. Similarly, Mg(OH)$_2$ has very low solubility in water because Mg$^{2+}$ has small ionic radii and therefore bonding Mg—O has high covalent character.

The subject monomeric compounds can provide for desirable uptake or absorption by a subject. In some cases, the monomeric compounds provide for a desirable bioavailability, e.g., as compared to conventional salt forms of HCA that may be dimeric or oligomeric. In some instances, KMgHCA when contacted with a suitable aqueous solution, can dissociate into, e.g., K$^+$ and [MgHCA]$^−$. In certain cases, MgHCA$^−$ can be easily transported into a cell as a small ionic species with a small electric charge. In certain instances, a mixture of KMgHCA and KCaHCA may provide increased solubility of the compounds in water. In certain instances, such compounds and mixtures of compounds can form an intermediate (e.g., in situ) such as a trimetal HCA compound (3), a five membered ring containing compound (4) or a coordinating OH ligand (5), as shown below. It is understood that under suitable conditions, a 5-membered version (i.e., analogous to compound (4)

below) of any one of the bimetal compounds described herein, may be prepared and utilized in the subject compositions and methods.

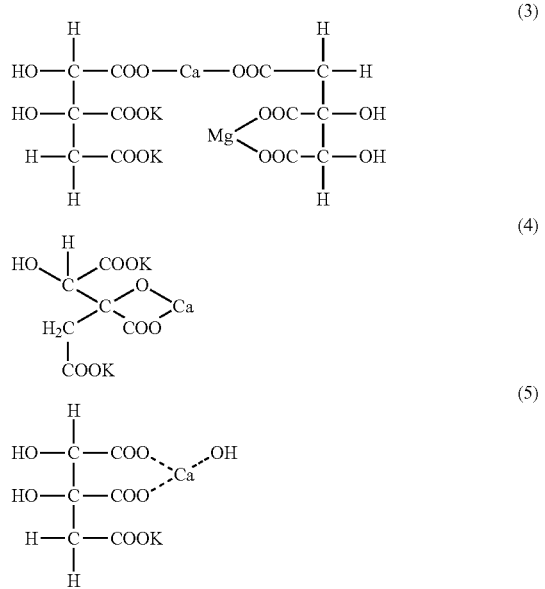

Aspects of the present disclosure include monomeric bimetal HCA compounds (e.g., as described herein), solvates, hydrates and/or prodrug forms thereof. In addition, it is understood that, in any compound described herein having one or more chiral centers (e.g., the C1 or C2 carbon centers), if an absolute stereochemistry is not expressly indicated, then each center may independently be of R-configuration or S-configuration or a mixture thereof. It will be appreciated that all permutations solvates, hydrates, prodrugs and stereoisomers are meant to be encompassed by the present disclosure.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

In some embodiments, the subject compounds are provided in the form of a solvate (e.g., a hydrate). The term "solvate" as used herein refers to a complex or aggregate formed by one or more molecules of a solute and one or more molecules of a solvent. Such solvates can be crystalline solids having a substantially fixed molar ratio of solute and solvent. Representative solvents include by way of example, water, methanol, ethanol, isopropanol, acetic acid, and the like. When the solvent is water, the solvate formed is a hydrate.

Also provided are compound active pharmaceutical ingredient compositions including a subject monomeric bimetal HCA compound (e.g., as described herein). As used herein, an active pharmaceutical ingredient refers to a composition that is produced using the subject methods of preparation, where the composition may optionally be subjected to one or more further purification steps post synthesis. In general, an active pharmaceutical ingredient is a composition suitable for formulation into a pharmaceutical composition. In some cases, the compound active pharmaceutical ingredient composition is not purified post synthesis, such that the components of the composition reflect those products produced during the subject methods of preparation. In some embodiments, the subject active pharmaceutical ingredient consists of a substantially pure monomeric HCA compound (e.g., as described herein). In some embodiments, the substantially pure monomeric HCA compound is the principle component of the subject active pharmaceutical ingredient. As used herein, by "substantially pure" is meant a composition having a purity of 80% or more, such as 85% or more, 90% or more, 95% or more, 98% or more or 99% or more with respect to a target component, e.g., a subject HCA compound.

Pharmaceutical Compositions

Also provided are pharmaceutical compositions that include a subject monomeric bimetal HCA compound. Pharmaceutical preparations are compositions that include a monomeric bimetal HCA compound (for example one or more of the subject compounds, either alone or in the presence of one or more additional active agents) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the compounds and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient will be determined in part by the particular compound, as well as by the particular method used to administer the composition. Accordingly, there is a wide variety of suitable formulations of the subject pharmaceutical compositions.

Administration of the subject compounds may be systemic or local. In certain embodiments administration to a mammal will result in systemic release of a compound of the present disclosure (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the compounds and compositions of the present disclosure are administered subcutaneously. In certain embodiments, the compounds and compositions of the present disclosure are administered orally. In certain embodiments, it may be desirable to administer one or more compounds of the present disclosure locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host. In pharmaceutical dosage forms, the compounds may be administered alone or in appropriate association, as well as in combination, with other pharmaceutically active compounds.

Dose levels can vary as a function of the specific compound, the nature of the delivery vehicle, and the like. Desired dosages for a given compound are readily determinable by a variety of means. The dose administered to an animal, particularly a human, in the context of the present disclosure should be sufficient to effect a prophylactic or therapeutic response in the animal over a reasonable time frame, e.g., as described in greater detail herein. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

Also provided are pharmaceutical preparations of the subject compounds and the second active agent. IN some instances the second active agent is a second monomeric bimetal HCA compound (e.g., as described herein). In pharmaceutical dosage forms, the compounds may be administered in a pharmaceutically acceptable form, or they may also be used alone or in appropriate association, as well as in combination, with other pharmaceutically active compounds.

Dosage levels of the order of from about 0.01 mg to about 140 mg/kg of body weight per day are useful in representative embodiments, or alternatively about 0.5 mg to about 7 g per patient per day. Those of skill will readily appreciate that dose levels can vary as a function of the specific compound, the severity of the symptoms and the susceptibility of the subject to side effects. Dosages for a given compound are readily determinable by those of skill in the art by a variety of means.

The amount of active ingredient(s) that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, such as 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Nutraceutical and Cosmetic Compositions

Also provided are nutraceutical compositions including one or more of the subject compounds. The nutraceutical composition can be administered as an oral liquid or solid dosage form. Oral solid dosage forms are well known in the art and include tablets, caplets, gelcaps, capsules, and edible food items. Oral solid dosage forms can be made with one or more pharmaceutically acceptable excipients. Pharmaceutically acceptable excipients assist or make possible the formation of a dosage form for a bioactive material and include diluents, binding agents, lubricants, glidants, disintergrants, coloring agents, and flavorants and nutrients. An excipient is pharmaceutically acceptable if, in addition to performing its desired function, it is non-toxic, well tolerated upon ingestion, and does not interfere with absorption of bioactive materials. In one aspect, the present disclosure is directed to an oral liquid dosage form including the nutraceutical composition and one or more vehicles and optional ingredients (e.g., as described herein). In another aspect, the present disclosure is directed to an oral solid dosage form that can be a tablet, a caplet, a gelcap, or a capsule that includes the nutraceutical composition and, optionally, one or more pharmaceutically acceptable excipients as is known in the art. Exemplary nutraceutical compositions and components of interest include those described in WO/2010/128949.

Also provided are cosmetic compositions including one or more of the subject compounds. Additional cosmetically or pharmaceutically beneficial ingredients can also be included in the formulated compositions of the present disclosure, which can be selected from, but not limited to skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antimicrobial agents, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, luffa particles, polyethylene balls, mica, pH adjusters, processing aids, and combinations thereof.

In some instances, the cosmetically acceptable composition further comprises one or more excipient selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about C10 to C22, long chain fatty amines from about C10 to C22, fatty alcohols, ethoxylated fatty alcohols and di-tail phospholipids. Emollients are defined as agents that help maintain the soft, smooth, and pliable appearance of skin. Emollients function by their ability to remain on the skin surface or in the stratum corneum. The cosmetically acceptable composition of this present disclosure may include fatty ester emollients, which are listed in the International Cosmetic Ingredient Dictionary, Eighth Edition, 2000, p. 1768 to 1773.

Methods of Use

Aspects of the present disclosure include methods for modulating a variety of diseases states of interest by administration of a subject monomeric bimetal HCA compound (e.g., as described herein) or a composition thereof. The subject compounds are monomeric and present in a form that provides for uptake and bioavailability of the compounds in vivo. In some cases, the uptake of the compounds is comparable to that observed for lactone forms of HCA. However, the subject compounds are in a desirable biologically active form suitable for use in the subject therapeutic methods.

In some aspects, methods for alleviating at least one symptom associated with a disease state, disorder or condition of interest are provided. In some embodiments, the subject methods are methods of preventing or treating the disease state, disorder or condition of interest. Diseases and conditions of interest include those where modulation of the physiological and biochemical effects of (−)-HCA are of interest, e.g., as described by Jena et al. (Chemistry and Biochemistry of (−)-Hydroxycitric Acid from *Garcinia*." Journal of Agricultural and Food Chemistry 50(1):10-22) and Clouatre et al. (US20050032901). In some cases, conditions where the inhibition of ATP citrate lyase, inhibition of metalloproteases (e.g., Zn proteases), selective inhibition of matrix metalloproteases (see e.g., Gupta et al US Patent 20060074108), conditions related to lipid abnormalities, or metabolic diseases or conditions, are of interest.

Target diseases and conditions of interest that may be modulated or treated according to the subject methods include any convenient disease or condition where administration of HCA finds use, including but not limited to, an obesity-related condition, diabetes, an inflammatory condition, osteoarthritis, hypertension, osteoporosis, wound healing, immunomodulation, metabolic dysfunction, metabolic diseases (e.g., metabolic/insulin-resistance syndrome, type 2 diabetes) and cardiovascular disease.

In some instances of the subject methods, the target disease or condition is an obesity-related condition. Administration of the subject compounds and compositions can enhance weight loss of the subject. In some cases, the subject compounds are weight control agents that can suppress appetite and/or food intake of the subject. In certain instances, the subject is obese. In some cases, the subject can achieve a weight loss of 5% or more, such as 10% or more, 15% or more, 20% or more, 25% or more, or even more, following administration of a subject monomeric bimetal HCA compound, or composition thereof.

In some instances of the subject methods, the target disease or condition is an inflammatory condition. Inflammation is linked to the metabolic syndrome at the cellular level by way of damage to the antioxidant-defense enzyme system and mitochondria. This damage, in turn, can propagate further production of pro-inflammatory mediators Inflammatory conditions of interest include, but are not limited to, chronic inflammatory diseases (e.g., cardiovascular disease), cancer, multiple sclerosis (MS), experimental autoimmune encephalomyelitis (EAE), oxidation stress related conditions. HCA can be useful as a protecting factor against diseases associated with oxidative stress, see e.g., Goudarzvand et al., "Hydroxycitric acid ameliorates inflammation and oxidative stress in mouse models of multiple sclerosis" Neural Regen Res. 2016 October; 11(10): 1610-1616).

In some instances of the subject methods, the target disease or condition is osteoarthritis. In some instances of the subject methods, the target disease or condition is osteoporosis. HCA can act to increase mineral retention and reduce bone loss induced by glucocorticoid-related mechanisms, see e.g., Clouatre et al. U.S. Pat. No. 6,441,041. Symptoms of interest that can be ameliorated according to the subject methods include, but are not limited to, pain, joint inflammation, loss of joint fluid, immobility of joints, legs or fingers, decreased bone density and calcification. Calcification is a term that refers to the accumulation of calcium salt in a body tissue at one location. In some cases calcifications may formed by strong chelating on protein site for example with Ca. Calcification may cause reduced cell and nerve activity. Calcification can be reduced using the subject HCA compounds. Calcified myosin has been decalcified in present of EDTA as a chelator. In a similar way, calcification can be treated using HCA and HCA compounds.

In some aspects, the present disclosure is directed to methods for inhibiting the symptoms or conditions (disabilities, impairments) associated with the target disease or condition as described in detail above. As such, it is not required that all effects of the condition be entirely prevented or reversed, although the effects of the presently disclosed methods likely extend to a significant therapeutic benefit for the patient. As such, a therapeutic benefit is not necessarily a complete prevention or cure for a particular condition or disease, but rather, can encompass a result which includes reducing or preventing the symptoms that result from the condition or disease, reducing or preventing the occurrence of such symptoms (either quantitatively or qualitatively), reducing the severity of such symptoms or physiological effects thereof, and/or enhancing the recovery of the individual after experiencing symptoms.

As used herein, the phrase "alleviating at least one symptom associated with" a disorder, disease, or condition (e.g., as described herein) denotes reversing, inhibiting the progress of, or preventing the disorder or condition to which such term applies, or reversing, inhibiting the progress of, or preventing one or more symptoms of the disorder or condition to which such term applies. Specifically, a composition of the present disclosure (such as any of the monomeric bimetal HCA compounds disclosed herein), when administered to an individual, can treat or prevent one or more of the symptoms or conditions associated with the target disease or condition and/or reduce or alleviate symptoms of or conditions associated with these disorders. As such, protecting an individual from the effects or symptoms resulting from the target disease or condition includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such patients in those who have been treated with the methods of the present disclosure as compared to those that have not.

The methods provided herein can also be practiced in a "neoadjuvant setting," i.e., the method can be carried out before the primary/definitive therapy. In some embodiments, the individual has previously been treated. In some embodiments, the individual has not previously been treated. In some embodiments, the treatment is a first line therapy.

As used herein, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of compound administered can be determined using any convenient methods to be an amount sufficient to produce the desired effect in association with a pharmaceutically acceptable diluent, carrier or vehicle. The specifications for the unit dosage forms of the present disclosure will depend on the particular compound employed and the effect to be achieved, and the pharmacodynamics associated with each compound in the host.

In some embodiments, an effective amount of a subject compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a subject compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the compound is administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Any of a variety of methods can be used to determine whether a treatment method is effective. For example, a biological sample obtained from an individual who has been treated with a subject method can be assayed for the presence and/or level of cells including a biomarker of the target disease or condition. Assessment of the effectiveness of the methods of treatment on the subject can include assessment of the subject before, during and/or after treatment, using any convenient methods. Aspects of the subject methods further include a step of assessing the therapeutic response of the subject to the treatment. In some embodiments, the method includes assessing the condition of the subject, including diagnosing or assessing one or more symptoms of the subject which are associated with the disease or condition of interest being treated (e.g., as described herein).

Methods of Preparation

Aspects of the present disclosure include methods for preparing a monomeric hydroxycitric acid (HCA) compound (e.g., as described herein). The subject method of preparation provides for monomeric forms of HCA that include two metals. A first step of the subject methods includes the isolation of a first divalent metal in a 7-membered heterocyclic ring of a monomeric compound, where the C2 and C3 carboxylate groups are bonded to the divalent metal, and the C1 carboxylate is converted to a free acid. The bonding of the HCA carboxylate groups to the divalent metal can be characterized as having substantial covalent character. In some cases, the first step includes acidifying a dimeric or oligomeric HCA compound including the target divalent metal, e.g., $X_3(HCA)_2$, under acidic conditions sufficient to produce a monomeric HX(HCA) having a particular configuration. In certain cases, acidification is achieved using an aqueous solution of a strong acid, e.g., sulfuric acid. In certain instances of the method, the HX(HCA) intermediate monomeric compound is isolated and dried prior to neutralization according to a second step of the method.

In a further step of the method a second monovalent metal is bonded with the free carboxylic acid group at C1 of the monomeric metal intermediate. In some cases, the second monovalent metal is installed via addition of an amount of YOH basic reagent sufficient to neutralize the free acid at C1 position. In some cases, the relatively lower (i.e., more acidic) pKa of the C1 versus the C3 carboxylic acid group can direct installation of the monovalent metal preferentially at that C1 position when the acidification and neutralization steps of the subject methods are performed in sequence starting from a suitable dimeric or oligomeric precursor. As such, the subject methods provide for a particular configuration of metal-HCA bonds to produce a monomeric bimetal HCA compound (e.g., as described herein).

The subject methods of preparation can proceed without formation of an undesirable mixture of dimeric and/or oligomeric HCA forms. The subject methods can also provide for preparation of monomeric bimetal compounds without formation of significant amounts of a lactone form of HCA. Exemplary methods and materials for practicing the subject methods of preparation are described in the experimental section below.

In some embodiments, the method comprises:

a) acidifying dimeric $X_3(HCA)_2$ with an acidic solution under conditions sufficient to produce a monomeric HX(HCA) compound of the formula:

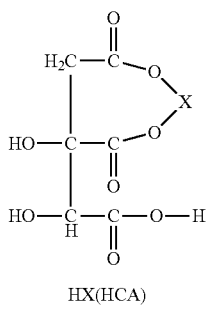

HX(HCA)

wherein X is a divalent metal;
b) neutralizing the monomeric HX(HCA) compound with a YOH solution under conditions sufficient to produce a monomeric hydroxycitric acid (HCA) compound of formula (I):

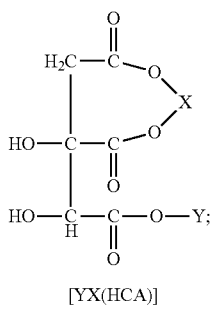

[YX(HCA)]

wherein Y is a monovalent metal; and
c) isolating the monomeric hydroxycitric acid (HCA) compound.

In some cases, X is selected from Group IIA metals, Group IIB metals and Group VIIA metals. The method can further comprise, prior to step b), isolating and drying the monomeric HX(HCA) compound. Unless stated otherwise the nomenclature YX(HCA) refers to a subject compound, e.g., of formula (I) or a precursor thereof.

In some instances, the method further comprises, prior to step a), contacting a sample comprising a monovalent metal HCA compound (e.g., $K_3HCA$) with a salt of the metal X to produce a dimeric $X_3(HCA)_2$ or an oligomeric form thereof. The subject precursor compounds and methods can be selected to minimize the presence or formation of lactone forms of the HCA compounds. The acidification, drying and/or neutralization steps of the subject methods can provide for formation of a monomeric bimetal HCA compound without formation of lactone or dimeric or oligomeric forms of HCA to contaminant the product composition. IN some cases, the subject compound composition that is isolated at the end of the subject methods is substantially pure (e.g., 80% purity or more, etc.).

In certain embodiments of the subject methods, a compound of formula (I) is produced where X is selected from Mg, Ca, Sr, Zn and Mn; and Y is selected from Li, Na and K. In certain cases, Y is Li. In some cases, Y is Na. In some cases, Y is K. In some cases, X is Mg. In some cases, X is Ca. In some cases, X is Sr. In some cases, X is Zn. In some cases, X is Mn. In some cases, the HCA is (−)-hydroxycitric acid.

The following examples are offered by way of illustration and not by way of limitation.

EXPERIMENTAL

Example 1: Preparation of Monomeric KMgHCA from $K_3HCA$

Syrup containing $K_3HCA$ (approximately 40.40% by wt) or HCA (25.72% by wt) was used in the method. The syrup further includes impurities such as gum, fiber, pectin, and garcinol etc. To prepare a HCA compound of interest from the syrup, several steps are performed:
1. Conversion of $K_3HCA$ to $Mg_3HCA_2$;
2. Acidification of $Mg_3HCA$ solution; and
3. Neutralization.
This method was also performed using HCA compositions from Laila as starting material.
Materials:
a. Syrup $K_3HCA$ was made according to conventional methods. HCA content of the syrup was determined by HPLC and found to be 25.72%.
b. $K_3HCA/Mg_3HCA$ donated by Laila company, India.
c. $MgCl_2.7H_2O$, $CaCl_2.2H_2O$, HCl 37%, $H_2SO_4$ conc. from EMerck.
Procedure:
1. Conversion $K_3HCA$ to $Mg_3(HCA)_2$
$K_3HCA$ syrup was placed into a 3 liter beaker glass and diluted with distilled water. The solution has pH 11. To the solution was then added a solution of $MgCl_2.7H_2O$ (0.791 mol., 182.8 g) in distilled water (350 mL). The mixture was warmed for 1 hour and then evaporated to a third of the volume (500 ml). After cooling overnight, crude crystals of $Mg_3HCA$ (120.7 g) formed and were isolated by filtration. HCA content of the crystals was 76.36% by HPLC. Characterization with FT IR(KBr) shows $\upsilon$ ($cm^{-1}$) 3237 br., 1579, 1391 $cm^{-1}$. Ion chloride is free.
2. Acidification of $Mg_3(HCA)_2$
Dried powder of $Mg_3(HCA)_2$ (100 g) was dissolved in hot distilled water 285 ml in a 1 liter glass beaker. A solution of 5% sulfuric acid (7.14 mL concentrated sulfuric acid in 375.14 mL distilled water) was added drop wise with vigorous stirring for 2 hours. After concentration of the solution volume to 100 ml, ethanol 200 ml then was added. The solution was reduced in volume to 50 ml then cooled to 5° C. for 5 hours to give a white solid which was isolated (75.112 g) by filtration. The melting point of the solid was 179° C. Characterization of the solid with FT-IR(KBr) shows $\upsilon$ 3295 br, 1620, 1402 $cm^{-1}$. No sulphate ion content. The compound is identified as 3-carboxylic, 1,2-magnesium chelate hydroxyl citric acid (HMgHCA).
3. Preparation KMgHCA
A solution of HMgHCA (73 g) was dissolved in 200 ml distilled water to give a resulting pH 3 solution. To this solution was added a solution of 20% KOH in distilled water until a pH of 11 was achieved. The solution was warmed for 1 hour, and then further heated to evaporate the solution and produce a solid. The solid formed was washed with ethanol. The solid was dried in a desiccator to give a yield of 70.12 g.
Characterization of the solid: FT-IR shows $\upsilon$, 3410, 1589, 1396 $cm^{-1}$. HCA content is 60.40% by HPLC. K content is 11.45% and Mg content is 7.06% using AAS. The remainder is hydrate at 21.17%. TGA analysis of KMgHCA is shown in FIG. 1. The melting point is 195° C. clear.

4. Determination $SO_4^{-2}$ Content

A 1.0 g sample of KMgHCA was placed in a crucible, and heated at 850° C. to achieve a constant weight. The residue was dissolved in distilled water (25 mL) and a solution of $BaCl_2$ titrated with oxalic acid was added.

5. Determination $Cl^-$ Content

A 1.0 g sample of KMgHCA was placed in a crucible, and heated at 850° C. to a constant weight. The residue was dissolved in distilled water (25 mL) and titrated with a solution of silver nitrate.

Result and Discussion a. Formation of $Mg_3HCA$

The syrup was low content $K_3HCA$ therefore initially HCA was converted primarily to $Ca_3HCA$ by addition $CaCl_2$ solution to adjust to pH 9. Crude $Ca_3HCA$ was then acidified with dilute sulfuric acid to bind calcium ions and release HCA in the aqueous phase. The HCA was then reverted to a dilute $K_3HCA$ and reacted with $MgCl_2$ to form $Mg_3(HCA)_2$ as crystals after concentrating the solution. This form provided high purity HCA useful in the subject methods.

b. Formation of 1-Carboxylic, 2,3-Magnesium Chelate Hydroxy Citric Acid (HMgHCA).

$Mg_3(HCA)_2$ obtained using the methods described above was dissolved and acidified with dilute sulfuric acid. A white solid isolated was characterized using FT-IR which showed three principal peaks $\upsilon(cm^{-1})$ 3295 br, 1620 and 1582. At band frequency 3800-3000 $cm^{-1}$ the broad peak is characteristic of a COOH group, however the band frequency of OH secondary alcohol usually at 3400 $cm^{-1}$ broad with low intensity. Because the peak created by the COOH group was so wide the OH group peak does not appear. A compound of HCA exhibits C=O vibration stretching at about 1580 $cm^{-1}$ and C=O acid at about 1600 $cm^{-1}$ (slightly broad), therefore the resulting bands are overlapping and appear together. This is because the C=O group was supported by the COOH group and $COO^-$ from Mg bonding.

Based on these results, the reaction mechanism is shown below for the formation of HMgHCA (1-carboxy-2,3-magnesium chelate hydroxycitric acid):

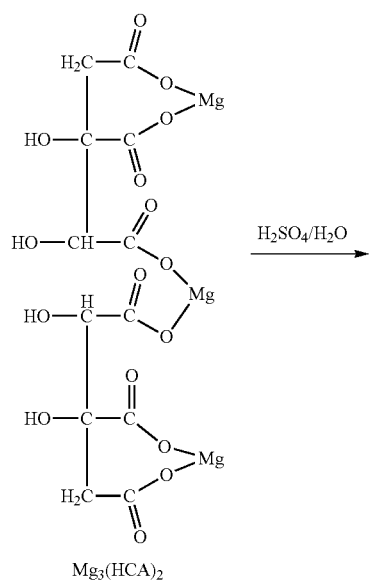

$Mg_3(HCA)_2$

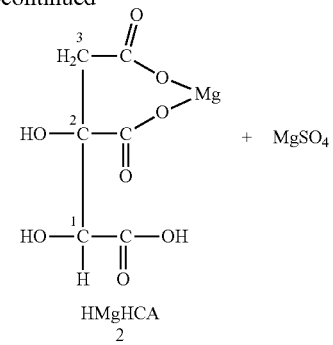

HMgHCA
2 c. Formation of Magnesium Potassium Bimetal HCA Compound.

Since HMgHCA (2) has a free acid, a neutralization process provides clear direction for installing the potassium ion at that position. The above mechanism shows that the K metal ion forms a bond with the COOH group at carbon atom number 1 as shown in the structure below:

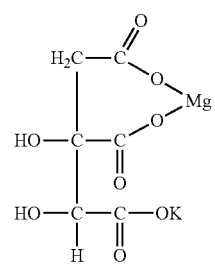

Potassium Magnesium Bimetal HCA Compound
(Monomeric KMgHCA)

Analysis of the monomeric KMgHCA product shows an HCA content of 60.40% by HPLC, K is 11.45% and Mg is 7.06% using AAS. The remainder is hydrate 21.17%. This number is confirmed via data with TGA analysis. The ratio mole calculation is $K:Mg:HCA:H_2O=1:1:1:4$ gives $KMgHCA.4H_2O$.

Example 2: Preparation of Monomeric KMgHCA

Procedure:

a. In a 500 ml glass beaker, pure acid form of HCA is diluted with distilled water. Calculate number of carboxylic group. Check mol. ratio of HCA free acid to HCA lactone.

b. Add a solution of KOH using a half equivalent relative to HCA acid, and react for a period of 0.5, 1.0 or 1.5 h. Each reaction is analyzed using HPLC to obtain a molar ratio of HCA acid in the reaction mixture.

c. The optimum condition gives the least amount of lactone, prior to adding $Mg(HCO_3)_2$ to the product mixture. The resulting product is highly soluble in water. By crystallization fractionation, monomer KMgHCA is recovered.

d. The product is purified and characterized using x-ray diffraction (XRD) as compared to a pure monomeric KMgHCA sample.

Example 3: Alternative Methods for Preparing Monomeric KMgHCA

1. Method of making $H_3HCA$ from $K_3HCA$ syrup.
   Take 100 gr of $K_3HCA$ (brix 74) consisting of 81% $K_3HCA$
   Dilute with 250 ml of demineralized water ("DMW")
   Add solution of $CaCl_2.2H_2O$ (56.0 g; 0.38 mol) into 100 ml of DMW
   The precipitate is taken out, washed, dried and $Ca_3(HCA)_2$ white powder is obtained
   The amount of white powder $Ca_3(HCA)_2$ is 70.78 g with 20.9% of Ca
   Mix the powder and 500 ml of DMW, producing a slurry
   The slurry is then loaded onto an acid cation resin exchange column
   The soluble eluate/filtrate is then loaded onto a strong anion exchange column.
   The product soluble eluate/filtrate (420 ml) is cleaned using activated carbon 1 g at 60° C. to give a clean HCA free acid.

2. Quality of the HCA Free Acid Solution
   The eluate/filtrate obtained above is then concentrated under reduced pressure at 60° C. to give a residue.
   The residue was extracted using dry acetone followed by dry ether.
   The insoluble part yields a white solid.
   The filtrate part is evaporated to dry. There is almost no significant residue (indicating very little lactones is formed)
   The white solid part is analyzed using HPLC and doesn't show any lactones 3. Method of Making Monomeric KMgHCA
   The process of making $H_3HCA$ is repeated as described in section above and HCA free acid is obtained
   250 ml of a solution having 0.1 mol $H_3HCA$ is obtained
   $Mg(OH)_2$ slurry (5.8 g; 0.1 mol) in 10 ml of DMW is added and the mixture left for 2 hours
   A solution of KOH (5.6 g; 0.1 mol) in 10 ml of demineralized water (DMW) is added. The pH of the mixture is observed to be 9-9.5
   20 ml of ethanol is added into this solution and 2 layers form.
   The top layer is separated, then ethanol added to achieve 70% ethanol.
   The bottom layer is separated and dried under vacuum
   A white solid is obtained, and washed using dry methanol
   White dry solid (20.0 g; 48.5%). Consisting of Mg 5.8%; K 9.42%. This analysis is close to theoretical for the formula $KMgHCA.8H_2O$ 4. Method of Making Monomeric KMgHCA
   The process of $H_3HCA$ making is repeated as described in section above and HCA free acid is obtained
   200 ml of a solution consisting of 0.1 mol $H_3HCA$ is obtained
   The $H_3HCA$ is partially neutralized using a solution of KOH (5.6 g; 0.1 mol) in 10 ml demineral water.
   Into the solution, a $Mg(OH)_2$ slurry (5.8 g; 0.1 mol) is added to form a white suspension.
   The mixture is heated at 60° C. for 1 hour, producing a clear solution
   The pH of the solution is adjusted to pH 9 by addition of a KOH solution. Then 20 ml of alcohol is added resulting in 2 layers.
   The top layer is separated and a further portion of ethanol added resulting in a solution of approximately 70% ethanol. This mixture forms 2 layers.
   The bottom layer is separated, then dried under vacuum, and then washed using dry methanol
   Dried insoluble material gave 35.5 g of white powder (86.2%) consisting Mg5.9% and K9.6%. This analysis is close to the formula of $KMgHCA.8H_2O$ 5. Method of making monomeric KMgHCA using $MgCl_2$
   10 g of $K_3HCA$ syrup (brix 74) consisting of 81% $K_3HCA$ is obtained
   Dilute with 20 ml of DMW
   Bleached with activated carbon (2 g in 20 ml of DMW), filtered.
   Take 40 ml of solution consisting $K_3HCA$ (8.1 g, 0.025 mol)
   Add solution of $MgCl_2.6H_2O$ (5.075 g; 0.025 ml) into 10 ml of DMW
   Into the reaction mixture, add in 60 ml of ethanol (98% pure)
   Stir for 1 day period, then remove the upper layer
   Add 300 ml of ethanol 98% to the upper layer solution. Stir for 1 day to extract Cl
   The upper layer solution containing Cl is then removed and the bottom layer is extracted by adding 100 ml of ethanol 98%
   Filtrate is separated, and insoluble part is dried under vacuum resulting a white powder.
   The powder is washed with dry methanol, and dried. The solid product is 7.0 g (67%) consisting K 9.5% and Mg 5.8% this is likely $KMg HCA.8H_2O$ 6. Method of making monomeric KMgHCA using strong anion resin
   20 g of $K_3HCA$ syrup (brix 74) consisting 81% $K_3HCA$ (16.2 g; 0.05 mol $K_3HCA$)
   Dilute with 100 ml of DMW
   Bleach with 4 g of activated carbon and filter out solids
   Filtrate is made into pH 5.5 using additional HCl
   This solution is loaded onto an anion exchange column, (strong anion resin type)
   A solution consisting of $KH_2HCA$ containing partially substituted $K^+$ was obtained
   $Mg(OH)_2$ slurry 0.025 mol was added and then heated at 60° C. give a solution.
   The solution consist of KMgHCA (see section 4)

7. Method of making of $H_3HCA$ from $K_3HCA$ syrup.
   In another method, the process begins with fresh fruit to produce a $K_3HCA$ syrup and then proceeds to through the production of $H_3HCA$ to the production of a monomeric KMgHCA as follows using a $Mg(OH)_2$ method:
   100 g of $K_3HCA$ (brix 74) consisting of 81% $K_3HCA$
   Dilute with 250 ml of demineralized water
   Add solutions of $CaCl_2.2H_2O$ (56.0 g; 0.38 mol) into 100 ml of DMW
   The precipitate is taken out, washed, dried and $Ca_3(HCA)_2$ white powder is obtained
   The amount of white powder $Ca_3(HCA)_2$ is 70.78 g with 20.9% of Ca
   Mix the powder and 500 ml of DMW, producing a dough
   The dough is then filled into acid cation exchange column
   Extracted soluble is then passed into strong anion exchange column.
   Producing Cl which consisted in cation exchange regeneration
   Product of soluble is 420 ml. Then it is cleaned using activated carbon 1 g in 60° C.
   Filtrate which is obtained is then concentrated using vacuum
   This concentrated liquid is extracted using dry eterasetone The insoluble part became white solid
Filtrate part is steamed until it is dried. There's almost no residue (indicating very little lactone formation is happening)
White solid part is tested in HPLC, doesn't show any lactones 8. KMgHCA monomer making
The process of $H_3HCA$ making is repeated and HCA free acid is obtained
250 ml of the solution are having 0.1 mol $H_3HCA$
Add $Mg(OH)_2$ dough (5.8 g; 0.1 mol) into 10 ml of DMW and leave it for 2 hours
Then KOH solution (5.6 g; 0.1 mol) is added into 10 ml of DMW. The pH is 9-9.5
20 ml of alcohol is added into this soluble and it forms 2 layers
Top layer is separated, then it's changed into ethanol 70%
Bottom layer is separated, steamed in vacuum
White solid is obtained, and being washed using dry methanol
We obtain white dry solid (20.0 g; 48.5%). Consisting Mg 5.8%; K 9.42%. $KMgHCA.8H_2O$

Example 4: Preparation of $Ca_3(HCA)_2$, HCaHCA, KCaHCA

Figure 2:
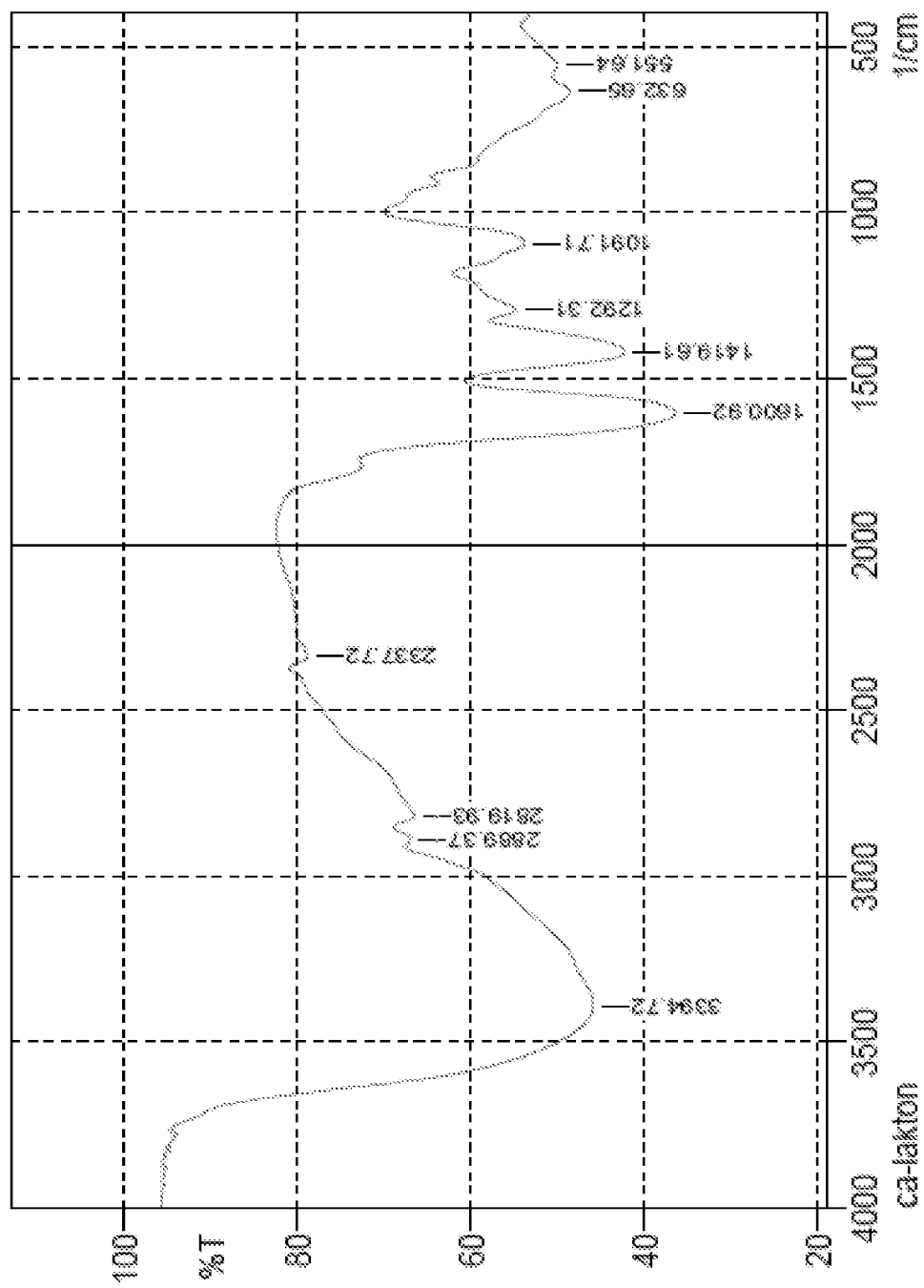
FIG. 2 shows an FT-IR spectrum of an exemplary monomeric KCaHCA compound.

1. Preparation of KCaHCA
The preparation is involving in 3 steps:
a. Preparation $Ca_3(HCA)_2$
A solution containing 78.4 gram, 0.24 mole $K_3HCA$ was made up to 500 ml. By addition slowly of the solution $CaCl_2$ 50% the solution mixture reaches a pH of 8 while stirring. The solid formed was filtered, washed with water to free chloride. The solid was dried, and provided 62.25 grams of $Ca_3(HCA)_2$.
b. Preparation of HCaHCA
62.25 grams $Ca_3(HCA)_2$ was suspended in water. The pH was adjusted to 5 by adding a solution of 0.05 N sulfuric acid. The solution was separated from the solid. Then evaporated to ⅓ volume. The mixture is then refiltered. The solution obtained is solidified after the addition of ethanol 450 ml. The amorphous solid was isolated by filtration, and washed with ethanol 200 ml, allowed to dry in air for 5 hours and finally dry in vacuum. The solid obtained was 60.25 grams of HCaHCA.
FT-IR spectrography (see FIG. 2) indicates that no lactone was present, and the HCA content of the composition is analyzed by HPLC.
Sample HCaHCA
9.86 mg HCaHCA in 10 ml buffer solution $(NH_4)_2HPO_4$ 10 mM. Peak area was 1367.4 or equal to 739.5349 ppm.
HCA=10/1000×739.5349 mg=7,395349 mg., HCaHCA=246/205×7,395=8.868 mg % HCA=7.395/9.86× 100%=75%
No lactone detected.
b. Neutralization of HCaHCA
60 g HCaHCA is dissolved in water then neutralized by the addition of a solution of KOH 20% to pH=11. Ethanol 150 ml is added to the solution mixture which then formed a white solid precipitate. After filtration, the white precipitate is dried in vacuum, to provide a solid yield of 63.5 grams.
The FT-IR spectrograph shows peaks 3549, 3402, 3244, 2233, 2117, 1685, 1620, 1134, 1002, 667, 601 $cm^{-1}$. The HCA product is analyzed by HPLC and TGA to give % weight of water.

11.08 mg KCaHCA is dissolved in 10 ml buffer solution $(NH_4)_2HPO_4$ and gave HPLC area total of 1226.2 equal to 663.1693 ppm. So, HCA=10/1000×663.1693 mg=6,663 mg KCaHCA=284/205×6,663=9.2306 mg
% HCA by HPLC was =6,663/11.08×100%=60.1%
TGA shown $H_2O$ water content 15.97%,
The HCA via HPLC is 60.1%. Ca=12.2%, K=11.7%. The formula is $KCaHCA.3H_2O$

Example 5: Preparation of $Zn_3(HCA)_2$, CZnHCA, KZnHCA

Introduction

The chemical reactions in the preparation of KZnHCA were described as below:

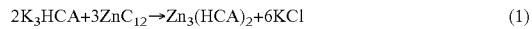

$2K_3HCA+3ZnC_{12} \rightarrow Zn_3(HCA)_2+6KCl$ (1)

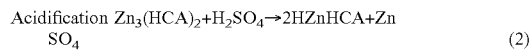

Acidification $Zn_3(HCA)_2+H_2SO_4 \rightarrow 2HZnHCA+ZnSO_4$ (2)

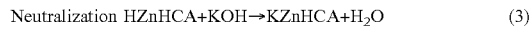

Neutralization $HZnHCA+KOH \rightarrow KZnHCA+H_2O$ (3)

b. Conversion $K_3HCA$ to $Zn_3(HCA)_2$
Into a 2 liter beaker glass, $K_3HCA$ solution 100 gr containing 11.2% $K_3HCA$ or equal to 11.2 grams, 0.0348 mol $K_3HCA$ was placed in a beaker glass. The solution was increased in volume up to 250 ml by the addition with distilled water. A solution of $ZnCl_2$ 20% was added slowly, until the pH was reduced to 5. The solid precipitated, was then filtered. The obtained precipitate was washed with distilled water two times until free of chloride. The solid was dried in a vacuum desiccators yielding 11 gr. M.P 174° C. dec.
The spectroscopy FT-IR showed wave number υ ($cm^{-1}$) 3441 slight broad shows OH secondary group, 1570 ($COO^-$) as fully salt, other peaks 1404, 1257, 1080, 918 and 860. The product was identified as $Zn_3(HCA)_2$.
TGA analysis of $Zn_3(HCA)_2$ is performed. From the analysis TGA obtained 2 molecules $H_2O$ or 6.61%. HCA contain 61.92%. Analysis SSA found Zn=30.45%
HPLC Analysis
11 mg $Zn_3(HCA)_2$ was placed in a 10 ml volumetric flask, then dissolved in 10 ml buffer solution $(NH_4)_2HPO_4$ to have 10 mM.
HPLC analysis shown the area observed was 2169.578 it was equal to 685.7073 ppm. The percentage of HCA in $Zn_3(HCA)_2$=685.7073 ppm/1100.0 ppm×100%=61.97%.
Based on the data results Zn=30.45%, HCA=61.97% (HPLC), $H_2O$=5.62% (TGA), the formula can be describe as $Zn_3(HCA)_2.2H_2O$. MW estimated 642.17
c. Acidified of $Zn_3HCA$ to Give HZnHCA
9 grams dried powder $Zn_3(HCA)_2$ was dissolved in 100 ml distilled water then added HCl 11% to pH=~3. Stirred until dissolved all, then filtered. Into the filtrate, 100 ml ethanol was added. The solid formed was filtered, dried on vacuum, the product obtained 7 gram. M.p 140° C. dec. The FT-IR spectrograph shows wave numbers υ 3437 $cm^{-1}$ (OH acid and OH secondary group), 1700-1612 $cm^{-1}$ (COO acid coupling to COOM, as salt), other peaks 1404, 1288, 1068, 910 and 540. The solid was determined to be HZnHCA.
TGA analysis of HZn(HCA) is performed. From the analysis via TGA it was determined the compound included 3 molecules $H_2O$ or 16.6%. HCA content 60.31%.
d. Preparation ZnKHCA
A solution of HZnHCA 5 g was dissolved in aqua double distilled 150 ml resulting pH 4. To this solution was added a solution of KOH 20% in aqua double distilled to give a pH 11. The solution was warmed for 1 hour, 50 ml ethanol then added resulting in a white solid precipitate. After filtration, the solid was dried in a desiccator to yield 5.5 g.

The FT-IR spectrograph shows wave number υ at 3500-3000 cm-1 seem containing hydrated in the solid; at approx 1577 cm$^{-1}$ shown all COO groups bound to metals; other peaks include 1396, 1296, 1072, 864 and 636 cm$^{-1}$.

Determine HCA Content Using HPLC 14.95 mg KZnHCA was placed in a 10 ml volumetric flask, then dissolved in 10 ml buffer solution $(NH_4)_2HPO_4$ gives 10 mM. HPLC analysis shows that the area observed was 2690.923 which was equal to 850.4814 ppm. The percentage of HCA in KZnHCA=850.4814 ppm/1495.0 ppm×100%=56.87%.

The TGA analysis of KZnHCA is performed. From the TGA analysis was obtained 2 molecules $H_2O$ or 10.43%, HCA contain 56.87% with RT 2.863 minutes, Analysis by Atomic Absorption Spectroscopy indicates Zn=18.8% and K=11.30%.

Sample ZnKHCA 14.30 mg KZnHCA was placed in a 10 ml volumetric flask, then dissolved in 10 ml buffer solution $(NH_4)_2HPO_4$ 10 mM. HPLC analysis shown the area observed was 2690.923 it was equal to 850.4814 ppm. The percentage of HCA=850.4814 ppm/1430.0 ppm×100%=59.47%.

The data results: K=11.30%., Zn=18.79%., HCA=59.47% and $H_2O$=10.43% is closed to mole ratio 1:1:1:2. The formula $ZnKHCA.2H_2O$.

Analysis of HCA Content

1. Preparation of HCA Standard Solution a. Primary standard (solution of 1000 ppm $Ca_3(HCA)_2$)

10 mg $Ca_3(HCA)_2.2H_2O$ was dissolved in 10 ml solution buffer $(NH_4)_2HPO_4$ 10 m M. The solution containing 1000 ppm of $Ca_3(HCA)_2$ or containing HCA=773,584 ppm b. Solution of 800 ppm $Ca_3(HCA)_2$ 8 ml of solution a was pipetted to a 10 ml volumetric flask, then diluted with 10 ml solution buffer $(NH_4)_2HPO_4$ mM. This solution containing $Ca_3(HCA)_2$=800 ppm or containing HCA=618,8679 ppm c. Solution of 400 ppm $Ca_3(HCA)_2$ 4 ml of solution a was pipetted to a 10 ml volumetric flask, then diluted with a 10 ml solution buffer $(NH_4)_2HPO_4$ mM. This containing $Ca_3(HCA)_2$=400 ppm or containing HCA=309,433 ppm.

d. Solution of 200 ppm $Ca_3(HCA)_2$ 2 ml of solution a was pipetted to a 10 ml volumetric flask, then diluted with a 10 ml solution buffer $(NH_4)_2HPO_4$ mM. This containing $Ca_3(HCA)_2$=200 ppm or contains HCA=157,716 ppm

TABLE 1

Concentration of HCA as Standard $Ca_3(HCA)_2$ vs Area

| No | Concentration HCA (mg/L or ppm) | Area |
|---|---|---|
| 1 | 309.433 | 1073.705 |
| 2 | 618.8679 | 1875.359 |
| 3 | 773.584 | 2435.800 |

A graphic representation of the data shows a linear function graph, and the HCA concentration of samples can be calculated by substituting the observed area.

Preparation of Samples

1. Sample $Zn_3(HCA)_2$ 11 mg $Zn_3(HCA)_2$ was placed in a 10 ml volumetric flask, then dissolved in 10 ml buffer solution $(NH_4)_2HPO_4$ 10 mM. HPLC analysis shown the area observed was 2169.578 it was equal to 685.7073 ppm. The percentage of HCA in $Zn_3(HCA)_2$=685.7073 ppm/1100.0 ppm×100%=61.97%.

2. Sample $Mn_3(HCA)_2$ 11.9 mg $Mn_3(HCA)_2$ was placed in a 10 ml volumetric flask, then dissolved in 10 ml buffer solution $(NH_4)_2HPO_4$ 10 mM. HPLC analysis shown the area observed was 2261.905 it was equal to 714.8878 ppm. The percentage of HCA in $Mn_3(HCA)_2$=714.8878 ppm/1190.0 ppm×100%=60.06%.

3. Sample HMnHCA 12.69 mg HMnHCA was placed in a 10 ml volumetric flask, then dissolved in 10 ml buffer solution $(NH_4)_2HPO_4$ 10 mM. HPLC analysis shown the area observed was 2847.079 it was equal to 899.8353 ppm. The percentage of HCA in CMnHCA=899.8353 ppm/12690.0 ppm×100%=70.79%.

4. Sample HZnHCA 16.77 mg HZnHCA was placed in a 20 ml volumetric flask, then dissolved in 20 ml buffer solution $(NH_4)_2HPO_4$ 10 mM. HPLC analysis shown the area observed was 1604.815 it was equal to 507.2108 ppm. The percentage of HCA in HZnHCA=507.2108 ppm/840.79 ppm×100%=60.31%.

5. Sample KZnHCA 14.95 mg KZnHCA was placed in a 10 ml volumetric flask, then dissolved in 10 ml buffer solution $(NH_4)_2HPO_4$ 10 mM. HPLC analysis shown the area observed was 2690.923 it was equal to 850.4814 ppm. The percentage of HCA in KZnHCA=850.4814 ppm/1495.0 ppm×100%=56.87%.

6. Sample KMnHCA 21.6 mg KMnHCA was placed in a 20 ml volumetric flask, then dissolved in 20 ml buffer solution $(NH_4)_2HPO_4$ 10 mM. HPLC analysis shown the area observed was 1989.482 it was equal to 628.787 ppm. The percentage of HCA in KZnHCA=628.787 ppm/1080 ppm×100%=58.19%.

Supplementary HPLC Data

Column: Chromolith High Resolution RP-18encapped, 100×4.6 mm

Mobile Phase: 10 Mm $(NH_4)_2HPO_4$ (pH=2.7)

Flow rate: 1 μL/10 mm

Injection volume: 20 μL

Run Time: 5 minutes

Temperature: 30° C.

Detector: UV, 210 nm

Gas pressure drop: 32 bar

Graphs are obtained to prepare a calibration curve for analysis of samples.

Example 6: Preparation of $Mn_3(HCA)_2$, CMnHCA, KMnHCA

Preparation of KMnHCA

Introduction

The chemical reactions in the preparation of KMnHCA were described as below:

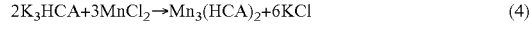

$2K_3HCA+3MnCl_2 \rightarrow Mn_3(HCA)_2+6KCl$ (4)

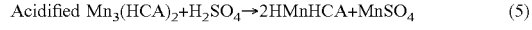

Acidified $Mn_3(HCA)_2+H_2SO_4 \rightarrow 2HMnHCA+MnSO_4$ (5)

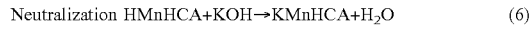

Neutralization $HMnHCA+KOH \rightarrow KMnHCA+H_2O$ (6)

Conversion $K_3HCA$ to $Mn_3(HCA)_2$ 116 g $K_3HCA$ solution, containing 22,258 gr., 0.0654 mol $K_3HCA$ was added to a solution made from 160 ml dry ethanol and $MnCl_2.2H_2O$ (16 g, 0.0981 mol) to give, pH=5.

The mixture was warmed for 30 minutes. After addition of a further 50 ml dry ethanol and settling for 5 minutes, a pink precipitate was formed, filtered, and washed with dry ethanol. $Mn_3(HCA)_2$ was dried under vacuum wet 22.8 gram. M.p 200° C. dec.

FT-IR spectrographic data for $Mn_3(HCA)_2$ presented highly water content due to wave number 3500-2770 $cm^{-1}$; other peaks included 3838, 3741, 1558, 1408, 1064, 910, 852 and 632 $cm^{-1}$. Water could be take place in the secondary valance of $Mn^{2+}$. This was taken to the further reaction before purification.

TGA analysis of $Mn_3(HCA)_2$ is performed. TGA analysis obtained 3 molecules $H_2O$ or 8.58% and HCA content of 60.06%.

Potentiometric titration found Mn=26.23%.

HPLC analysis was performed to determine the HCA concentration.

11.9 mg $Mn_3(HCA)_2$ was placed in a 10 ml volumetric flask, then dissolved in 10 ml buffer solution $(NH_4)_2HPO_4$ 10 mM. HPLC analysis shown the area observed was 2261.905 it was equal to 714.8878 ppm. The percentage of HCA in $Mn_3(HCA)_2$=714.8878 ppm/1190.0 ppm×100%=60.06%.

Results Mn=26.23%., HCA=60.06% and $H_2O$=8.58%. The formula is $Mn_3(HCA)_2.3H_2O$.

Acidification of $Mn_3HCA_2$ 30 grams of $Mn_3(HCA)_2$ wet (20 gr $Mn_3(HCA)_2$) added 100 ml distilled water and stirred. Then is added a solution of HCl 11% to pH=5. Then filtered. Filtrate was added dry ethanol 150 ml then filtered to form a solid precipitate. The precipitate was dried obtained 26 gr. Solubility HMnHCA in water 3.3 gram in 100 ml water.

A spectrograph of FT-IR is obtained which indicated that no lactone groups were present, and TGA analysis of HMnHCA is performed.

TGA analysis obtained molecule $H_2O$ or 6.3%. Mn content was determined using potentiometric titration and found Mn=19.78%.

HCA content was 70.79%, based on HPLC analysis: 12.69 mg HMnHCA was placed in a 10 ml volumetric flask, then dissolved in 10 ml buffer solution $(NH_4)_2HPO_4$ 10 mM. HPLC analysis shown the area observed was 2847.079 it was equal to 899.8353 ppm. The percentage of HCA in HMnHCA=899.8353 ppm/12690.0 ppm×100%=70.79%.

Preparation of KMnHCA 20 grams HMnHCA was dissolved in 500 ml of distilled water followed by addition KOH ethanolic solution 20% to pH=7. Into the solution, 100 ml of dry alcohol was added to give a solid separated. The solid was isolated by filtration, washed with ethanol, dried in vacuum desiccators. The yield obtained 20.35 gr.

A spectrograph via FT-IR was obtained which shows that the compound may contain water and all the carboxyl groups.

TGA analysis of $MnK(KCA)_2$ is performed. TGA analysis obtained 2 molecules $H_2O$ or 10.14%.

HCA containing 58.19% based on HPLC as shown below.

Potentiometric titration indicated Mn content=16.4%,

An SSA analysis obtained showed K present at 11.64%.

Sample KMnHCA 21.6 mg KMnHCA was placed in a 20 ml volumetric flask, then dissolved in 20 ml buffer solution $(NH_4)_2HPO_4$ 10 mM. HPLC analysis showed the area observed was 1989.482; it was equal to 628.787 ppm. The percentage of HCA in KMnHCA=628.787 ppm/1080 ppm×100%=58.19%.

Based on the data bimetal formula is $KMnHCA.2H_2O$

Example 7: Characterization of Compounds

1. $Mg_3HCA_2$ Starting Material

1H NMR in D2O: Quartet at 2.7 ppm: coupling ~17 Hz and equal. ~1:3:3:1 ratio. Ratio of peak at 4.01 to quartet: ~2

$^1H$ NMR in H2O: Quartet at 2.7 ppm: coupling ~17 Hz but central peaks at ~15 Hz. ~1:4:4:1 ratio. Ratio of peak at 4.0 to quartet ~2.6. Extra peaks appear at ~1.6 and 1.5

Mass Spec: Mass at ~483 (+mode) consistent with: $C_{12}H_{10}Mg_3O_{16}$. Mol Wt 483.11, exact mass 481.95.

$^{13}C$ NMR spectrum ($H_2O$): 41.76, 75.70, 78.54, 78.59, 177.61, 178.35, 179.63 ppm.

2. KMgHCA Monomeric Bimetal Compound $^1H$ NMR in $D_2O$: Quartet at 2.7 ppm: coupling ~16 Hz outer peaks and 8 Hz inner peaks. ~1:4:4:1 ratio Ratio of peak at 3.9 ppm to quartet: ~2

Figure 3:
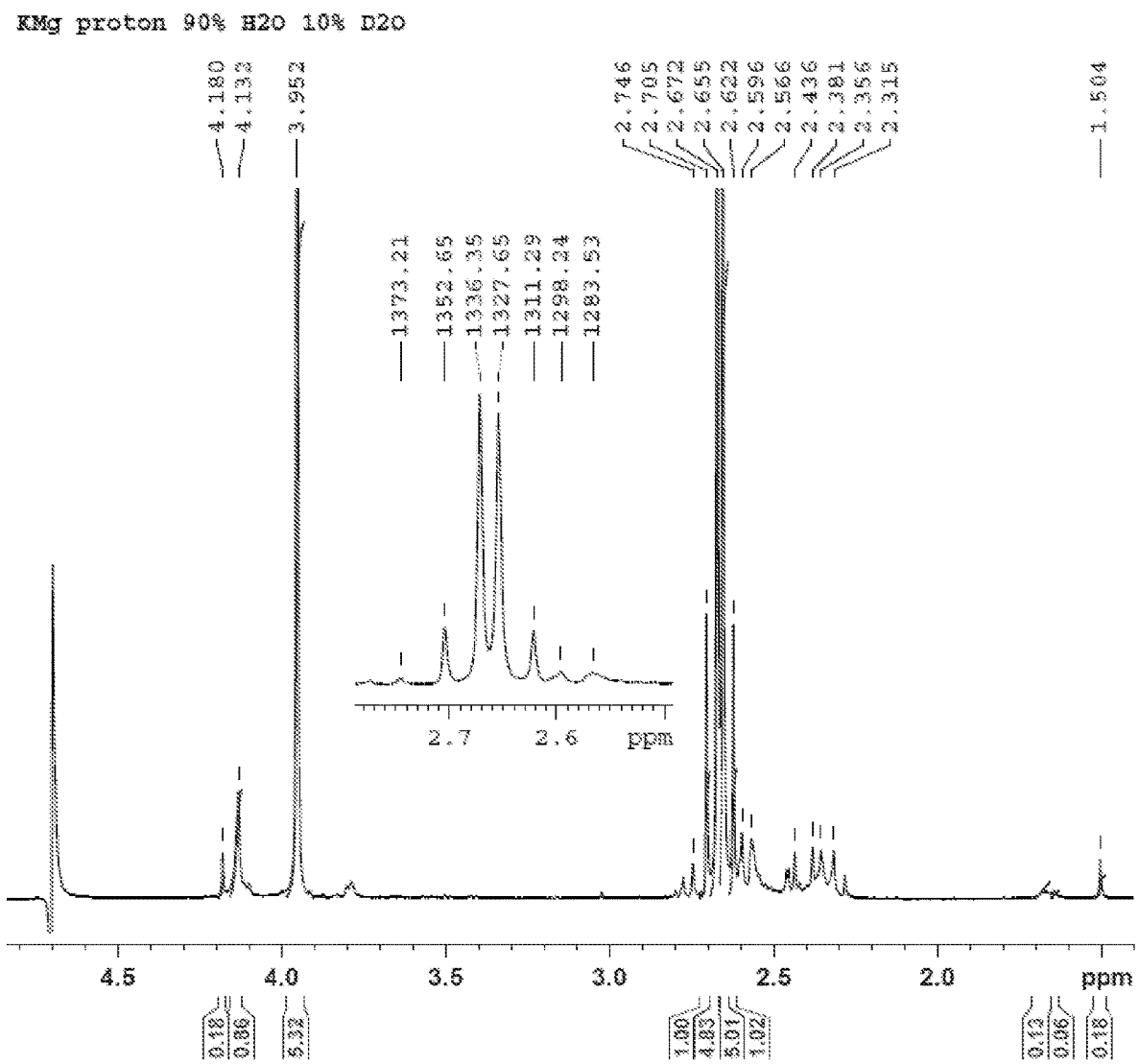
FIG. 3 illustrates an expanded portion of the $^1H$ NMR spectrum of a sample of exemplary compound KMgHCA.

$^1H$ NMR in $H_2O$: Quartet at 2.7 ppm: coupling ~16 Hz outer peaks and 8 Hz inner peaks. ~1:5:5:1 ratio. Ratio of peak at 3.9 ppm to quartet: ~2.2. Extra peaks appear at ~1.5 and 1.7. FIG. 3 illustrates a portion of the NMR spectrum.

$^{13}C$ NMR spectrum ($H_2O$): 42.23, 76.15, 78.51, 177.65, 178.71, 179.75 ppm.

3. KZnHCA Monomeric Bimetal Compound

Figure 4:
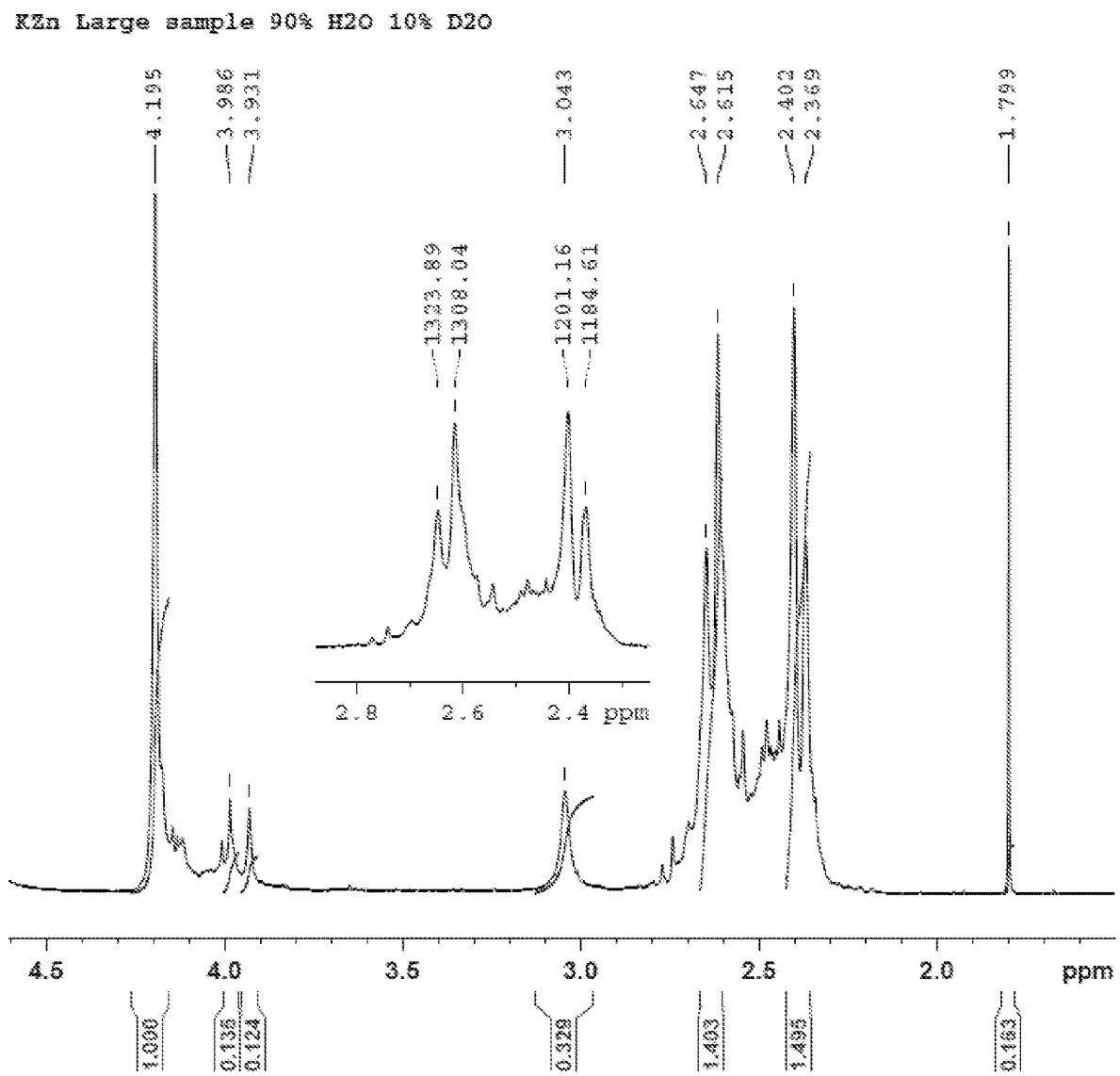
FIG. 4 illustrates an expanded portion of the $^1H$ NMR spectrum of a sample of exemplary compound KZnHCA.

1H NMR in H2O: Two doublets appear at ~2.4 and 2.6 ppm: coupling ~16 Hz. Ratio of peak at 3.9 ppm to quartet: ~2.8 (however, integral hard to establish because of peak overlap with other signals). FIG. 4 illustrates a portion of the NMR spectrum.

$^{13}C$ NMR spectrum ($H_2O$): 40.81, 43.25 (minor), 75.73, 76.39, 178.67, 178.89, 183.17 ppm.

Example 8: Conductivity of Solutions

The structure of the subject compounds (e.g., as described herein) can be deduced using a conductance meter to observe the extent of dissociate of the first and/or second metals from the compounds. In an experiment described below equimolar samples and comparative electrolyte conductance to K-acetate solution as a standard, data may be obtained which is characteristic of electrolyte binary conductants. By using a highly ionic compound, such as KCl, as a standard for conductivity in equimolar solutions, results show a similarity curve. The KMgHCA solution in water may have a pH 8-10 depending on the concentration. Under this condition, the heterocyclic anion formed will tend toward a stable form rather than an ionizable one.

In contrast, in a solution of $Mg_3(HCA)_2$, a dimeric HCA form, the ionic form will be available as a solution with a pH below 7. This can be dissolved in water by a dissolution process, meaning that $Mg_3(HCA)_2$ still presents as a dimer and not as a binary solution form.

Experiments

Several experiments investigating the electrical conductivities of solutions of KMgHCA, KZnHCA and KMnHCA were performed. The equipment used was HACH Conductivity/TDS meter, P/N=4460-00.

Materials: $KMgHCA.4H_2O$, $KZnHCA.2H_2O$, $KMnHCA.2H_2O$ were prepared using methods described herein. $KC_2H_3O_2$ and $Mg_3(CH_3O_2)_2.4H_2O$ was obtained from Merck. $H_2O$ used was demineralized water.

General procedure: All the HCA compounds and Acetate were weighed and placed in a volumetric flask and dissolved with demineralized water to one liter solution and then they were tested the conductivity (EC).

The data obtained is summarized below in Table 2:

| Run | Materials | Molecular weight | Weight (mg) | Concentration mmol/l | additive | E. C (µS/cm) |
|---|---|---|---|---|---|---|
| 1 | $KC_2H_3O_2$ | 98.15 | 29.4 | 0.3 | | 56.06 |
| 2 | $KMgHCA \cdot 4H_2O$ | 340.46 | 102.1 | 0.3 | — | 60.25 |
| 3 | $KMgHCA \cdot 4H_2O$ | 340.46 | 102.1 | 0.3 | 10 mg gliserol | 60.23 |
| 4 | $KMgHCA \cdot 4H_2O$ | 340.46 | 102.1 | 0.3 | 10 mg glucose | 60.29 |
| 5 | $KMnHCA \cdot 2H_2O$ | 335.10 | 100.5 | 0.3 | | 59.8 |
| 6 | $KZnHCA \cdot 2H_2O$ | 345.54 | 103.7 | 0.3 | | 57.7 |
| 7 | $Mg_3(HCA)_2 \cdot 2H_2O$ | 446.12 | 44.6 | 0.1 | | 31.2 |
| 8 | $Mg(CH_3COO)_2 \cdot 4H_2O$ | 214.46 | 64.3 | 0.3 | | 32.3 |

Results:
1. Contribution κ (value of electrical conductivity)
At the beginning study (run 1), it was necessary to know what was likely κ (value of electrical conductivity) resulting of ionic compound made of strong electrolyte with weak electrolyte such as $CH_3COOK$. This salt in water is dissociated completely gave κ=56.06 µS/cm.
2. Mg—O bond κ value
Run 2 shows the result 2 bond of Mg—O contribution approx 60.25-56.06 is 4.19 µS/cm. For 2 bond dissociate gave κ value contribution 2.095 in µS/cm. This low value is resulting by the dissociated degree much lower compared to K—O bond.
Since κ value is affected also by ionic charged, +2 higher than +1, then $Mg^{2+}$ should be given higher contribution to κ value $K^+$. It means that the solution has low concentration $Mg^{2+}$ and implies a low value of dissociation degree of Mg—O. As a conclusion, bonding Mg—O is likely covalent polar, low ionic degree.
3. Effect of OH Function
To check the electrical function of hydroxyl, then run 3 and 4 was done. There was not a significant change in κ value. Based on this result, the OH group in HCA has no direct effect on variations in κ value.
4. Effect of Zn and Mn in HCA
The qualitative ionization degree has a correlation to electrical conduction (κ values) in a solution. A lower κ values of a solution has a good indication lower ionic bond character in the matter. The experiment results shown run 5 and 6 gave κ values 59.8 and 57.7 in µS/cm for Mn and Zn respectively. This value is much lower compared to KMgHCA at the equal molar solution. Therefore Zn—O bond is more covalent polar than Mn—O and more covalent then Mg—O. The experiment 7 and 8 was made equimolar solution of $Mg^{2+}$. The result κ values were relatively low. The overall conclusion is bonding of Mg, Zn and Mn with O is likely covalent polar.
5. Theoretical View Ionic Bond Character
A most famous theory for ionic bond bond character was proposed by Hanny and Smyth. The equation is shown below:

$$\% \text{ ionic character in A-B bond} = [0.16(\chi_A - \chi_B) + 3.5(\chi_A - \chi_B)^2]\%$$

$\chi_A$ and $\chi_B$ are represented for electronegativity A and B element.
Compound KMgHCA is containing two covalent bond polar, K—O and Mg—O bond.

$$\text{Ionic character K—O} = [0.16(3.44 - 0.82) + 3.5(3.44 - 0.82)^2]\% \text{ eq to } = 24.45\%.$$

$$\text{Ionic character Mg—O} = [0.16(3.44 - 1.31) + 3.5(3.44 - 1.31)^2]\% \text{ eq to } = 16.22\%.$$

In a similar manner ionic character can be estimated for Mn—O and Zn—O bond found as 12.80 and 9.63% respectively.
Covalent character as conclusion K—O=75.55%., Mg—O=83.78%., Mn—O=87.20% and Zn—O=90.37%. This means that all heterocyclic rings have a covalent character.

Example 9: Weight Loss and Reduced Inflammation

Subject Complaint: Edema, pain in legs, darkening of skin
Subject and Treatment Summary:
1. Sex: Female
2. Age: 50 years
3. Weight before treatment: 60 kg
4. General health before treatment: fairly good
5. Medical complaints: lack of energy, bone of legs inflamed (painful) after walking
6. Bimetal HCA Regimen:—KMg HCA, KCa HCA mixed powder.
    Dosage: 200 mg, 3 times a day after meals
    either consumed with plain water or juice of pineapple, tomato—or simply chewed and swallowed
7. Side effects: none
8. Progressive change in patient: In second month of treatment, the patient reduce weight to 55 kg, in the third month reduced to 52 kg and pain/inflammation in legs reduced in frequency. In the sixth month reduce to 48 kg with inflammation gone.

A woman aged 50 years previously in fairly good health, developed edema in her legs and 60 kg overweight leading to inflammation in legs as well as some darkening of the skin. A mixture of 150 mg KMg HCA and 50 mg KCa HCA was administered 3 times per day in water for 120 days. During this period she lost 12 kg of weight and her legs condition return to normal. No side effects were reported.

Example 10: Treatment of Inflammation and Joint Damage in Knees

Subject and Treatment Summary:
1. Sex: Female
2. Age: 44 years
3. Weight before treatment: 90 kg
4. General health before treatment
    blood pressure 150/90
    HDL 1.4 mg/L
    LDL 2.6 mg/L
5. Specific medical complaint:
    High inflammation in her legs, mainly in her knees. During night, it was like flame in the whole legs. She required periodic injection of fluid into her knees.
6. Doctor's Diagnosis: X-ray left knee joint shows lost joint fluid. Degenerative changes are noted in the patella-femoral and knee joint. Multiple dense loose bodies are seen in the left knee joint. Narrowing of the knee joint space is noted.
7. Bimetal HCA Regimen:—150 mg KMg HCA and 50 mg Ca HCA powder
    3 times a day after meals
    Drink with juice, tomato, pineapple, strawberry.
8. No side effects 9. Progressive change to patient condition:
   Little reported reaction for 4 months. In the fifth month after initiation of treatment, a dramatic improvement in the legs was observed. Subsequently, a µ X-ray was obtained, which showed an increase in lubricating fluid in the left knee joint, indicating the joint was successfully treated although not yet completely healed. Blood pressure improved to the range of 140-130 over 90-80.

Results:
Women aged 44 year, 90 kg in weight along with knee joint problem. Her feeling was awful and medical diagnosis was losing fluid in knee joint. A mixture of bimetal HCA compounds 150 mg KMg HCA and 50 mg Ca HCA was administered 3 times per day in water for 120 days. During this period she has returned to normal in her legs. She reported good sleep. No side effects were reported.

Example 11: Treatment of Severe Osteoarthritis in Knees and Hands

Subject and Treatment Summary:
1. Sex: Female
2. Age: 86 years
3. Wight before treatment: 40 kg
4. General health: not available
5. Specific Medical Complaint: pain in joints of legs and fingers caused immobility
6. Doctor diagnosis: not available
7. Bimetal HCA Regimen:—KMg HCA, KCa HCA powder 100 mg to 150 mg
   2 times a day after meal ("chewed")
8. No side effects reported
9. Chronology of progressive change: After taking the preparation for 3 days, the pain disappeared totally and fingers could be moved freely. The sustainability was 3-7 days without consuming bimetal HCA before return of original complaint. Symptomatic relief returned soon after taking bimetal HCA.
10. No medical confirmation Notes:
The subject "chewed" aprpox. 100 mg of a mixture of the bimetal HCA compositions, morning and evening. Dosage was later increased to 150 mg twice a day. The subject's overall health and arthritis in her hands and knees is reported to be improved.

Example 12: Symptomatic Relief of Osteoarthritis in Legs

Subject and Treatment Summary:
1. Sex: Female
2. Age: 61 years,
3. Weight before treatment: 72 kg
4. General health: Uric acid 7.8 mg/dl; cholesterol 201 mg/dl
5. Specific medical complaint: subject cannot walk due to osteoartrosis genu bilateral in her legs
6. Bimetal HCA Regimen:—KMg HCA, KCa HCA powder 200 mg after meals
   3 times per day
   Consumed with juice
7. No side effects reported
8. Chronology of progressive change:
   in 3 days subject could stand on her feet
   in 10 days subject could walk
   in 14 days subject could do work
9. No medical report after healing

Example 13: Comparison of Different Bimetal Regimes (KMg Vs. KCa Vs. Combination)

Subject I: a women, 86 years, 40 kg (cited in Example 11, above)
Problem: osteoporosis and calcification on hand and leg (suspected); discomfort and greatly reduced use of hands/mobility
Subject II: a women, 69 years; 72 kg
Problem: osteoporosis and calcification on leg (doctor diagnosis); discomfort and greatly reduced mobility
Treatment: A. Mixture 25% KCa HCA+75% KMg HCA bimetals (100-200 mg)
B. Only KMg HCA bimetal
Results:

TABLE 1

| Patient | Treatment A | Treatment B |
|---------|-------------|-------------|
| I       | + +         | Not tested  |
| II      | + +.        | + −         |

+ +: very good performance
+ −: good but slight complaint
Treatment A: Administration of 100-200 mg of the mixed composition, 3 times a day (after meals) gave excellent reduction in symptoms for both subjects. Additional KCa HCA can be administered to treat a lack of calcium in blood and also to supply Ca to the subject for maintaining equilibrium of Ca for production of bone.
Treatment B: Only KMg HCA but not KCa HCA was used. Subject II reported partial reduction of symptoms. Subject II had slight complaint on her leg. Following treatment 2, the observed result was that she could stand on her feet.

Example 14: Comparison of KCaHCA and/or KMgHCA Compositions

Subject: Female (cited as Example 12, above)
Age: 61 years
Problem: Osteoporosis
Treatment: Materials were consumed 3 times a day after meals.
   Experiment 1. Blending 150 mg KMgHCA.8H$_2$O+50 mg KCaHCA.3H$_2$O
      A 200 mg mixture of KCaHCA (25%) and KMgHCA (75%) prepared according to the subject methods was used. The actual percentage of calcium was (40/338)×25%=2.96%. Since KCaHCA.3H$_2$O was used the percentage of magnesium in the composition was (24/412)×75%=4.37%. Since KMgHCA.8H$_2$O was used, the ratio Ca:Mg=0.15: 0.36 in mmol.
   Experiment 2. 200 mg KMgHCA.8H$_2$O
   Experiment 3. 200 mg KCaHCA.3H$_2$O
Results:
Experiment 1 gave very good results. In three days the subject could stand on her feet, in 10 days she could walk, in 14 days she could walk freely. The observation was continued for 3 months. In the fourth month, treatment by experiment 2 was started by administration of 200 mg doses of KMgHCA. The patient was slight difficult to walk because feeling of burning sensation in her feet. Subject complained that her leg felt hot. The experiment 2 regimen was continued for a month.
Subsequently (in the next month), treatment was continued according to experiment 3. The patient received 200 mg bimetal KCaHCA. Administration using experiment 3 conditions was continued for a few days, but was then stopped due to deterioration in subject's condition to the point that she became unable to move her leg. Treatment according to experiment 1 was started.

These results indicate that the patient experienced a reduction in symptoms of osteoporosis under treatment with 200 mg blended mixture of KCaHCA/KMgHCA (150 mg KMgHCA with 50 mg KCaHCA). In Experiment 2, the patient showed a partial improvement of symptoms of osteoporosis. Administration of KCaHCA alone in experiment 3 was not effective. Use of a blend of 150 mg KMgHCA with 50 mg KCaHCA is an excellent treatment for osteoporosis.

Although the particular embodiments have been described in some detail by way of illustration and example for purposes of clarity of understanding, it is readily apparent in light of the teachings of this invention that certain changes and modifications may be made thereto without departing from the spirit or scope of the appended claims.

Accordingly, the preceding merely illustrates the principles of the invention. Various arrangements may be devised which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

Notwithstanding the appended claims, the disclosure set forth herein is also described by the following clauses.

Clause 1. A compound of structural formula I:

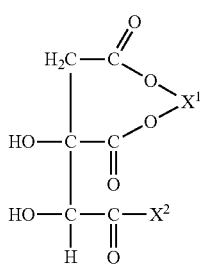

wherein $X^1$ and $X^2$ are independently any metal.

Clause 2. The compound of clause 1, wherein $X^1$ and $X^2$ are independently a metal selected from the group consisting of calcium, magnesium, manganese, sodium, potassium and zinc.

Clause 3. The compound of formula 1, wherein $X^1$ is magnesium (Mg) and $X^2$ is potassium (K).

Clause 4. The compound of structural formula (Ia)

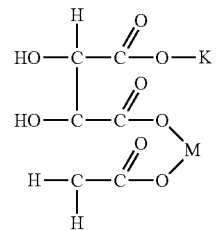

which compound is hydrated to obtain a compound of formula (II)

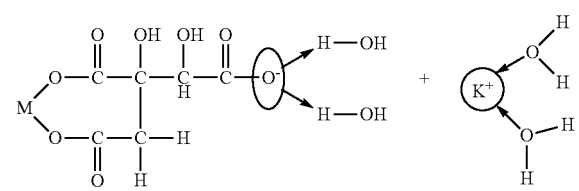

wherein M is any metal bonding to two oxygens.

Clause 5. A method of treatment, comprising:
administering to a subject in need of treatment a formulation comprising:
a carrier; and
a therapeutically effective amount of a compound of structural formula I

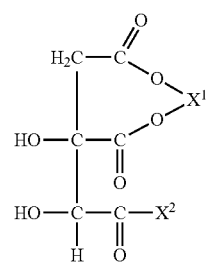

wherein $X^1$ and $X^2$ are independently any metal.

Clause 6. The method of clause 1, wherein $X^1$ and $X^2$ are independently a metal selected from the group consisting of calcium, magnesium, manganese, sodium, potassium and zinc.

Clause 7. The method of clause 5, wherein $X^1$ is magnesium (Mg) and $X^2$ is potassium (K).

Clause 8. A method of weight loss, comprising:
administering to a human in need of treatment a formulation comprising:
a carrier; and
a therapeutically effective amount of a compound of structural formula I

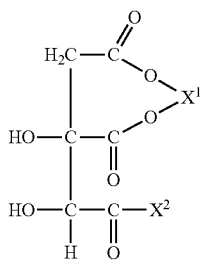

wherein $X^1$ and $X^2$ are independently any metal.

Clause 9. The method of clause 8, wherein $X^1$ and $X^2$ are independently a metal selected from the group consisting of calcium, magnesium, manganese, sodium, potassium and zinc.

Clause 10. The method of clause 8, wherein $X^1$ is magnesium (Mg) and $X^2$ is potassium (K).

Clause 11. The method of any of clauses 8-10 wherein the formulation comprises an amount of the compound of formula I of from 10 mg to 1,000 mg.

Clause 12. The method of any of clauses 8-10 wherein the formulation comprises an amount of the compound of formula I of from 100 mg to 500 mg.

Clause 13. The method of any of clauses 8-10 wherein formulation comprises an amount of the compound of formula I of 200 mg±20%.

Clause 14. The method of any of clauses 8-13 wherein the formulation is administered three times per day.

Clause 15. The method of clause 14 wherein the formulation is administered after meals. Notwithstanding the appended claims, the disclosure set forth herein is also described by the following clauses.

Clause 101. A monomeric hydroxycitric acid (HCA) compound of formula (I):

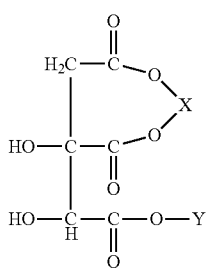

(I)

wherein:
X is a divalent metal (e.g., a metal selected from Group IIA metals, Group IIB metals and Group VIIA metals); and
Y is a monovalent metal;
or a hydrate thereof.

Clause 102. The monomeric HCA compound of clause 101, wherein X is a Group IIA group metal.

Clause 103. The monomeric HCA compound of clause 102, wherein X is selected from Mg, Ca, Sr, Ba and Ra.

Clause 104. The monomeric HCA compound of clause 101, wherein X is a Group IIB group metal.

Clause 105. The monomeric HCA compound of clause 104, wherein X is Zn.

Clause 106. The monomeric HCA compound of clause 101, wherein X is a Group VIIA group metal.

Clause 107. The monomeric HCA compound of clause 106, wherein X is Mn.

Clause 108. The monomeric HCA compound of clause 101, wherein Y is a Group IA metal.

Clause 109. The monomeric HCA compound of clause 108, wherein Y is selected from Li, Na and K.

Clause 110. The monomeric HCA compound of clause 109, wherein Y is K.

Clause 111. The monomeric HCA compound of clause 101, wherein:
X is selected from Mg, Ca, Sr, Zn and Mn; and
Y is selected from Li, Na and K.

Clause 112. The monomeric HCA compound of clause 111, wherein Y is Li.

Clause 113. The monomeric HCA compound of clause 111, wherein Y is Na.

Clause 114. The monomeric HCA compound of clause 111, wherein Y is K.

Clause 115. The monomeric HCA compound of any one of clauses 112-114, wherein X is Mg.

Clause 116. The monomeric HCA compound of any one of clauses 112-114, wherein X is Ca.

Clause 117. The monomeric HCA compound of any one of clauses 112-114, wherein X is Sr.

Clause 118. The monomeric HCA compound of any one of clauses 112-114, wherein X is Zn.

Clause 119. The monomeric HCA compound of any one of clauses 112-114, wherein X is Mn.

Clause 120. The monomeric HCA compound of any one of clauses 101-119, wherein the HCA is (−)-hydroxycitric acid.

Clause 121. An active pharmaceutical ingredient comprising a substantially pure monomeric HCA compound according to any one of clauses 101-120.

Clause 122. A pharmaceutical or nutraceutical composition, comprising:
a monomeric HCA compound according to any one of clauses 110-120, or an active pharmaceutical ingredient according to clause 121; and
a pharmaceutically acceptable excipient.

Clause 123. The pharmaceutical or nutraceutical composition of clause 122, further comprising a second monomeric HCA compound.

Clause 124. The pharmaceutical or nutraceutical composition of clause 123, wherein the second monomeric HCA compound is a compound according to any one of clauses 101-120.

Clause 125. The pharmaceutical or nutraceutical composition of clause 124, wherein the first and second monomeric HCA compounds are KCaHCA and KMgHCA.

Clause 126. A method of alleviating at least one symptom associated with a target disease or condition in a subject, the method comprising:
administering to a subject in need thereof an amount of a compound of any one of clauses 101-120, or a composition of any one of clauses 122-125, effective to alleviate at least one symptom associated with a target disease or condition;
wherein the target disease or condition is selected from an obesity-related condition, diabetes, an inflammatory condition, osteoarthritis, hypertension, osteoporosis, wound healing, immunomodulation, metabolic dysfunction and cardiovascular disease.

Clause 127. The method of clause 126, wherein the target disease or condition is an obesity-related condition.

Clause 128. The method of clause 127, wherein the subject is obese and achieves a weight loss of 5% or more (e.g., 10% or more, 15% or more, etc.) following administration of the monomeric HCA compound.

Clause 129. The method of clause 126, wherein the target disease or condition is an inflammatory condition.
Clause 130. The method of clause 126, wherein the target disease or condition is osteoarthritis or osteoporosis.
Clause 131. The method of clause 129 or 130, wherein the at least one symptom is selected from pain, joint inflammation, loss of joint fluid, immobility of joints, legs or fingers, decreased bone density and calcification.
Clause 132. The method of any one of clauses 126-131, wherein the monomeric HCA compound is selected from LiMgHCA, NaMgHCA, KMgHCA, LiCaHCA, NaCaHCA, KCaHCA, LiSrHCA, NaSrHCA, KSrHCA, LiZnHCA, Na7nHCA, KZnHCA, LiMnHCA, NaMnHCA and KMnHCA.
Clause 133. The method of any one of clauses 126-132, wherein the monomeric HCA compound is KMgHCA.
Clause 134. A method of preparing a monomeric hydroxycitric acid (HCA) compound, the method comprising:
a) acidifying dimeric $X_3(HCA)_2$ with an acidic solution under conditions sufficient to produce a monomeric HX(HCA) compound of the formula:

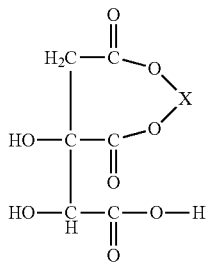

wherein X is a divalent metal (e.g., a metal selected from Group IIA metals, Group IIB metals and Group VIIA metals);
b) neutralizing the monomeric HX(HCA) compound with a YOH solution under conditions sufficient to produce a monomeric hydroxycitric acid (HCA) compound of formula (I):

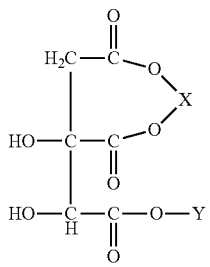

wherein X is a divalent metal and Y is a monovalent metal; and
c) isolating the monomeric hydroxycitric acid (HCA) compound.
Clause 135. The method of clause 134, further comprising, prior to step b), isolating and drying the monomeric HX(HCA) compound.
Clause 136. The method of any one of clauses 134-135, further comprising, prior to step a), contacting a sample comprising $K_3HCA$ with a salt of the metal X to produce the dimeric $X_3(HCA)_2$.

Clause 137. The method of clause 135, wherein the isolated monomeric hydroxycitric acid (HCA) compound is substantially pure (e.g., 80% purity or more, etc.).
Clause 138. The method of any one of clauses 134-137, wherein:
X is selected from Mg, Ca, Sr, Zn and Mn; and
Y is selected from Li, Na and K.
Clause 139. The method of clause 138, wherein Y is Li.
Clause 140. The method of clause 138, wherein Y is Na.
Clause 141. The method of clause 138, wherein Y is K.
Clause 142. The method of any one of clauses 139-141, wherein X is Mg.
Clause 143. The method of any one of clauses 139-141, wherein X is Ca.
Clause 144. The method of any one of clauses 139-141, wherein X is Sr.
Clause 145. The method of any one of clauses 139-141, wherein X is Zn.
Clause 146. The method of any one of clauses 139-141, wherein X is Mn.
Clause 147. The method of any one of clauses 134-146, wherein the HCA is (−)-hydroxycitric acid.

What is claimed is:
1. A covalent monomeric hydroxycitric acid (HCA) compound of formula (I):

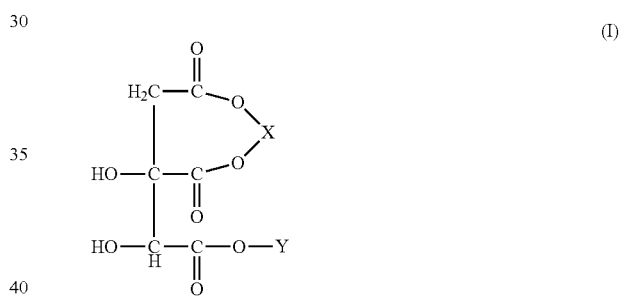

wherein:
X is a divalent metal selected from Group IIA metals, Group IIB metals or a divalent metal selected from Mn, Tc and Re; and
Y is a monovalent metal;
or a hydrate thereof,
wherein X—O and Y—O comprise covalent bonds.
2. The monomeric HCA compound of claim 1, wherein X is a Group IIA group metal.
3. The monomeric HCA compound of claim 2, wherein X is selected from Mg, Ca, Sr, Ba and Ra.
4. The monomeric HCA compound of claim 1, wherein X is a Group IIB group metal.
5. The monomeric HCA compound of claim 4, wherein X is Zn.
6. The monomeric HCA compound of claim 1, wherein X is a divalent metal selected from Mn, Tc and Re.
7. The monomeric HCA compound of claim 6, wherein X is Mn.
8. The monomeric HCA compound of claim 1, wherein Y is a Group IA metal.
9. The monomeric HCA compound of claim 8, wherein Y is selected from Li, Na and K.
10. The monomeric HCA compound of claim 1, wherein the HCA is (−)-hydroxycitric acid.

11. The monomeric HCA compound of claim 1, wherein:
X is Mg, Ca, Sr, Ba and Ra; and
Y is K.

12. The monomeric HCA compound of claim 1, wherein the compound has a melting point of 200° C. or less.

13. The monomeric HCA compound of claim 12, wherein the compound has a melting of from 160° C. to 200° C.

14. The monomeric HCA compound of claim 1, wherein:
X is selected from Mg, Ca, Sr, Ba and Ra; and
Y is selected from Li, Na and K,
wherein the compound has a melting point of 200° C. or less.

15. The monomeric HCA compound of claim 1, wherein:
X is selected from Mg, Ca, Sr, Ba and Ra; and
Y is selected from Li, Na and K,
wherein the compound has a melting point of from 160° C. to 200° C.

16. The monomeric HCA compound of claim 1, wherein thermogravimetric analysis (TGA) of the monomeric HCA compound is characterized by a weight loss step at about 250° C.

17. The monomeric HCA compound of claim 1, wherein the X—O bond and the Y—O bond each independently comprise 50% or more covalent character as determined by conductivity of an aqueous solution of the monomeric HCA compound.

18. The monomeric HCA compound of claim 1, wherein the X—O bond and the Y—O bond each independently comprise 70% or more covalent character as determined by conductivity of an aqueous solution of the monomeric HCA compound.

\* \* \* \* \*